United States Patent
Sharp et al.

(10) Patent No.: US 11,191,750 B2
(45) Date of Patent: Dec. 7, 2021

(54) USE OF MTOR INHIBITORS FOR TREATMENT OF FAMILIAL ADENOMATOUS POLYPOSIS

(71) Applicant: THE BOARD OF REGENTS OF THE UNIVERSITY OF TEXAS SYSTEM, Austin, TX (US)

(72) Inventors: Zelton Dave Sharp, San Antonio, TX (US); Randy Strong, San Antonio, TX (US); Paul Hasty, San Antonio, TX (US); Carolina Livi, San Antonio, TX (US); Arlan Richardson, San Antonio, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/915,506

(22) Filed: Jun. 29, 2020

(65) Prior Publication Data
US 2020/0330442 A1  Oct. 22, 2020

Related U.S. Application Data

(63) Continuation of application No. 15/337,410, filed on Oct. 28, 2016, now abandoned, which is a
(Continued)

(51) Int. Cl.
*A61K 31/436* (2006.01)
*A61K 31/415* (2006.01)
(Continued)

(52) U.S. Cl.
CPC .......... *A61K 31/436* (2013.01); *A61K 9/5138* (2013.01); *A61K 31/192* (2013.01); *A61K 31/415* (2013.01); *A61K 45/06* (2013.01)

(58) Field of Classification Search
CPC .. A61K 31/436; A61K 31/415; A61K 31/152; A61K 9/5138
See application file for complete search history.

(56) References Cited

U.S. PATENT DOCUMENTS

| | | |
|---|---|---|
| 3,929,992 A | 12/1975 | Sehgal et al. |
| 3,993,749 A | 11/1976 | Seghal et al. |

(Continued)

FOREIGN PATENT DOCUMENTS

| | | |
|---|---|---|
| CA | 2572100 | 6/2007 |
| CN | 1863509 | 11/2006 |

(Continued)

OTHER PUBLICATIONS

Anastas et al., "WNT signalling pathways as therapeutic targets in cancer." Nat Rev Cancer. vol. 13, No. 1, 2013, pp. 11-26.
(Continued)

*Primary Examiner* — Carlos A Azpuru

(57) ABSTRACT

Disclosed are methods and compositions for the treatment or prevention of intestinal polyps or prevention of cancer in a patient who has been identified as being at risk for developing intestinal polyps or intestinal cancer. The disclosed methods and compositions include rapamycin, a rapamycin analog, or another such inhibitor of the target of rapamycin (TOR).

20 Claims, 5 Drawing Sheets

Related U.S. Application Data continuation of application No. 14/775,291, filed as application No. PCT/US2014/026329 on Mar. 13, 2014, now abandoned.

(60) Provisional application No. 61/778,670, filed on Mar. 13, 2013.

(51) Int. Cl.
 *A61K 31/192* (2006.01)
 *A61K 9/51* (2006.01)
 *A61K 45/06* (2006.01)

(56) References Cited

U.S. PATENT DOCUMENTS

| | | |
|---|---|---|
| 4,316,885 A | 2/1982 | Rakhit |
| 4,401,653 A | 8/1983 | Eng |
| 4,460,722 A | 7/1984 | Igarashi et al. |
| 4,885,171 A | 12/1989 | Surendra et al. |
| 5,023,262 A | 6/1991 | Caufield et al. |
| 5,023,263 A | 6/1991 | Von Burg |
| 5,023,264 A | 6/1991 | Caufield et al. |
| 5,066,493 A | 11/1991 | Sehgal et al. |
| 5,078,999 A | 1/1992 | Warner et al. |
| 5,080,899 A | 1/1992 | Sturm et al. |
| 5,100,883 A | 3/1992 | Schiehser |
| 5,100,899 A | 3/1992 | Caine |
| 5,102,876 A | 4/1992 | Caufield |
| 5,118,677 A | 6/1992 | Caufield |
| 5,118,678 A | 6/1992 | Kao et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Faili et al. |
| 5,130,307 A | 7/1992 | Failli et al. |
| 5,138,051 A | 8/1992 | Hughes et al. |
| 5,151,413 A | 9/1992 | Caufield et al. |
| 5,162,333 A | 11/1992 | Failli et al. |
| 5,164,399 A | 11/1992 | Failli et al. |
| 5,169,851 A | 12/1992 | Hughes et al. |
| 5,177,203 A | 1/1993 | Failli et al. |
| 5,194,447 A | 3/1993 | Kao |
| 5,202,332 A | 4/1993 | Hughes et al. |
| 5,206,018 A | 4/1993 | Sehgal et al. |
| 5,221,670 A | 6/1993 | Caufield |
| 5,221,740 A | 6/1993 | Hughes |
| 5,233,036 A | 8/1993 | Hughes |
| 5,260,299 A | 11/1993 | Failli et al. |
| 5,260,300 A | 11/1993 | Hu |
| 5,262,423 A | 11/1993 | Kao |
| 5,262,424 A | 11/1993 | Kao |
| 5,286,731 A | 2/1994 | Caufield et al. |
| 5,288,711 A | 2/1994 | Mitchell et al. |
| 5,302,584 A | 4/1994 | Kao et al. |
| 5,310,903 A | 5/1994 | Goulet et al. |
| 5,321,009 A | 6/1994 | Baeder et al. |
| 5,344,833 A | 9/1994 | Hughes |
| 5,346,893 A | 9/1994 | Failli et al. |
| 5,358,944 A | 10/1994 | Caufield |
| 5,362,718 A | 11/1994 | Skotnicki et al. |
| 5,373,014 A | 12/1994 | Failli et al. |
| 5,378,696 A | 1/1995 | Caufield |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,446,048 A | 8/1995 | Faille et al. |
| 5,463,048 A | 10/1995 | Skotnicki et al. |
| 5,480,988 A | 1/1996 | Failli et al. |
| 5,480,989 A | 1/1996 | Kao et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,504,204 A | 4/1996 | Failli et al. |
| 5,504,291 A | 4/1996 | Goble et al. |
| 5,508,285 A | 4/1996 | Nelson et al. |
| 5,508,286 A | 4/1996 | Skotnicki et al. |
| 5,508,290 A | 4/1996 | Nelson et al. |
| 5,508,399 A | 4/1996 | Kao et al. |
| 5,516,780 A | 5/1996 | Skotnicki et al. |
| 5,519,031 A | 5/1996 | Skotnicki et al. |
| 5,521,194 A | 5/1996 | Nelson et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,541,191 A | 7/1996 | Skotnicki et al. |
| 5,541,192 A | 7/1996 | Skotnicki et al. |
| 5,550,133 A | 8/1996 | Failli et al. |
| 5,552,160 A | 9/1996 | Liversidge et al. |
| 5,559,112 A | 9/1996 | Skotnicki et al. |
| 5,559,119 A | 9/1996 | Skotnicki et al. |
| 5,559,120 A | 9/1996 | Kao et al. |
| 5,559,121 A | 9/1996 | Harrison et al. |
| 5,559,122 A | 9/1996 | Nelson et al. |
| 5,561,138 A | 10/1996 | Armstrong |
| 5,563,145 A | 10/1996 | Failli et al. |
| 5,567,709 A | 10/1996 | Skotnicki et al. |
| 5,575,987 A | 11/1996 | Kamei et al. |
| 5,637,590 A | 6/1997 | Skotnicki et al. |
| 5,665,772 A | 9/1997 | Cottens et al. |
| 5,780,462 A | 7/1998 | Lee et al. |
| 5,891,469 A | 4/1999 | Amselem |
| 5,912,253 A | 6/1999 | Cottens et al. |
| 5,922,730 A | 7/1999 | Hu et al. |
| 5,932,243 A | 8/1999 | Fricker et al. |
| 5,955,457 A | 9/1999 | Lee et al. |
| 5,985,890 A | 11/1999 | Cottens et al. |
| 5,989,591 A | 11/1999 | Nagi |
| 6,004,973 A | 12/1999 | Guitard et al. |
| 6,015,809 A | 1/2000 | Zhu et al. |
| 6,197,781 B1 | 3/2001 | Guitard et al. |
| 6,200,985 B1 | 3/2001 | Cottens et al. |
| 6,204,243 B1 | 3/2001 | Posanki |
| 6,228,396 B1 | 5/2001 | Watts |
| 6,329,386 B1 | 12/2001 | Mollison |
| 6,399,625 B1 | 6/2002 | Zhu |
| 6,440,990 B1 | 8/2002 | Cottens et al. |
| 6,475,518 B1 | 11/2002 | Baumgart et al. |
| 6,486,099 B2 | 11/2002 | Igari et al. |
| 6,503,883 B1 | 1/2003 | Posanki |
| 6,537,195 B2 | 3/2003 | Forman |
| 6,555,132 B1 | 4/2003 | Brox et al. |
| 6,569,463 B2 | 5/2003 | Patel et al. |
| 6,592,916 B2 | 7/2003 | Soeda et al. |
| 6,596,268 B1 | 7/2003 | Coffey et al. |
| 6,605,298 B1 | 8/2003 | Leigh et al. |
| 6,649,157 B2 | 11/2003 | Coffey et al. |
| 6,653,256 B1 | 11/2003 | Wolf et al. |
| 6,670,355 B2 | 12/2003 | Azrolan et al. |
| 6,677,357 B2 | 1/2004 | Zhu et al. |
| 6,680,330 B2 | 1/2004 | Zhu et al. |
| 6,849,651 B2 | 2/2005 | Danishefsky et al. |
| 6,923,988 B2 | 8/2005 | Patel et al. |
| 6,929,818 B2 | 8/2005 | Luthra et al. |
| 6,936,644 B2 | 8/2005 | Gilleo |
| 6,956,043 B2 | 10/2005 | Guitard et al. |
| 6,974,473 B2 | 12/2005 | Barclay et al. |
| 7,008,979 B2 | 3/2006 | Schottman et al. |
| 7,037,582 B2 | 5/2006 | Xing et al. |
| 7,041,046 B2 | 5/2006 | Forman |

(56) References Cited

U.S. PATENT DOCUMENTS

| | | |
|---|---|---|
| 7,084,171 B2 | 8/2006 | Grainer et al. |
| 7,132,458 B2 | 11/2006 | Burton et al. |
| 7,160,867 B2 | 1/2007 | Abel et al. |
| 7,220,755 B2 | 5/2007 | Betts et al. |
| 7,241,771 B2 | 7/2007 | Zhu |
| 7,268,144 B2 | 9/2007 | Gu et al. |
| 7,271,177 B2 | 9/2007 | Benjamin et al. |
| 7,273,874 B2 | 9/2007 | Graziani et al. |
| 7,279,562 B2 | 10/2007 | Molnar-Kimber |
| 7,282,505 B2 | 10/2007 | Zhu et al. |
| 7,292,885 B2 | 11/2007 | Scott et al. |
| 7,304,033 B2 | 12/2007 | Larsen et al. |
| 7,445,916 B2 | 11/2008 | Gu et al. |
| 7,446,111 B2 | 11/2008 | Benjamin et al. |
| 7,452,723 B2 | 11/2008 | Coffey et al. |
| 7,455,853 B2 | 11/2008 | Mollison et al. |
| 7,470,682 B2 | 12/2008 | Graziani et al. |
| 7,476,678 B2 | 1/2009 | Graziani et al. |
| 7,488,444 B2 | 2/2009 | Furst et al. |
| 7,511,070 B2 | 3/2009 | Grainger et al. |
| 7,517,342 B2 | 4/2009 | Scott et al. |
| 7,517,362 B2 | 4/2009 | Shanley et al. |
| 7,519,418 B2 | 4/2009 | Scott et al. |
| 7,538,119 B2 | 5/2009 | Gu et al. |
| 7,560,457 B2 | 7/2009 | Graziani et al. |
| 7,576,903 B2 | 8/2009 | Yamamoto et al. |
| 8,007,831 B2 | 8/2011 | Lewis et al. |
| 8,053,444 B2 | 11/2011 | Revin et al. |
| 9,700,544 B2 * | 7/2017 | Vail .............. A61K 9/1635 |
| 2001/0026807 A1 | 10/2001 | Watts |
| 2002/0009473 A1 | 1/2002 | Tebbe |
| 2003/0215496 A1 | 11/2003 | Patel et al. |
| 2004/0010002 A1 | 1/2004 | Wasik et al. |
| 2004/0074089 A1 | 4/2004 | Gilleo |
| 2004/0121155 A1 | 6/2004 | Matsunami et al. |
| 2005/0090553 A1 | 4/2005 | Shapiro |
| 2005/0113282 A1 | 5/2005 | Parekh et al. |
| 2006/0115533 A1 | 6/2006 | Guitard et al. |
| 2006/0121122 A1 | 6/2006 | Nakajima et al. |
| 2006/0210638 A1 | 9/2006 | Liversidge et al. |
| 2006/0234053 A1 | 10/2006 | Yamamoto et al. |
| 2006/0251720 A1 | 11/2006 | Penhasi et al. |
| 2006/0264453 A1 | 11/2006 | Mudumba et al. |
| 2007/0082829 A1 | 4/2007 | Smets et al. |
| 2007/0138673 A1 | 6/2007 | Lee et al. |
| 2007/0142423 A1 | 6/2007 | Graziani et al. |
| 2007/0185150 A1 | 8/2007 | Bedrosian |
| 2007/0203168 A1 | 8/2007 | Zhao |
| 2007/0203170 A1 | 8/2007 | Zhao |
| 2007/0203171 A1 | 8/2007 | Zhao |
| 2007/0203172 A1 | 8/2007 | Zhao |
| 2007/0225313 A1 | 9/2007 | Zhao |
| 2007/0280992 A1 | 12/2007 | Margaron et al. |
| 2008/0022965 A1 | 1/2008 | Bysreen et al. |
| 2008/0069797 A1 | 3/2008 | Roncarolo et al. |
| 2008/0085880 A1 | 4/2008 | Viswanath et al. |
| 2008/0091008 A1 | 4/2008 | Viswanath et al. |
| 2008/0138405 A1 | 6/2008 | Raheja et al. |
| 2008/0182867 A9 | 7/2008 | Wasik et al. |
| 2008/0188511 A1 | 8/2008 | Beckmann et al. |
| 2008/0193653 A1 | 8/2008 | Oh |
| 2008/0234380 A1 | 9/2008 | Shapiro |
| 2008/0249123 A1 | 10/2008 | Gu et al. |
| 2008/0275076 A1 | 11/2008 | Holm et al. |
| 2010/0150864 A1 | 6/2010 | Hickman et al. |
| 2011/0104256 A1 | 5/2011 | Wang et al. |
| 2011/0105387 A1 | 5/2011 | Wu et al. |
| 2011/0195966 A1 | 8/2011 | Garcia-Echeverria et al. |
| 2011/0293731 A1 | 12/2011 | Lewis et al. |
| 2012/0064143 A1 * | 3/2012 | Sharp .............. A61K 45/06 424/439 |
| 2012/0276169 A1 | 11/2012 | Choi et al. |
| 2013/0035343 A1 | 2/2013 | Porta et al. |

FOREIGN PATENT DOCUMENTS

| | | |
|---|---|---|
| WO | WO 1995/031194 | 11/1995 |
| WO | WO 2006/066063 | 6/2006 |
| WO | WO 2007/093346 | 8/2007 |
| WO | WO 2008/022256 | 2/2008 |
| WO | WO 2010/009335 | 1/2010 |
| WO | WO 2010/144846 | 12/2010 |

OTHER PUBLICATIONS

Austad, Steven, "Mixed Results for Dieting Monkeys," *Nature*, 2012; 489: 210-211.

Blagosklonny, "Aging and immortality: quasi-programmed senescence and its pharmacologic inhibition," Cell Cycle. 5(18):2087-102, 2006.

Blagosklonny, "An anti-aging drug today: from senescence-promoting genes to anti-aging pill," Drug Discov Today. 12(5-6):218-24, 2007.

Boulanger, et al., "Human Herpesvirus-8 (HHV-8)-Associated Primary Effusion Lymphoma in two Renal Transplant Recipients Receiving Rapamycin", Am J Transplant. 8:707-10, 2008.

Bulow, et al., "Duodenal adenomatosis in familial adenomatous polyposis", Gut. 53(3):381-6, 2004.

Campistol, "Minimizing the risk of posttransplant malignancy." Transplantation Proceedings, vol. 40, No. 10, Supplement, 2008, S40-S43.

Cao et al., "Toll-like receptor-mediated induction of type I interferon in plasmacytoid dendritic cells requires the rapamycin-sensitive PI(3)K-mTOR-p70S6K pathway," Nat Immunol. Oct. 2008;9(10):1157-64.

Carter et al., "Molecular mechanisms of life- and health-span extension: role of calorie restriction and exercise intervention," Appl Physiol Nutr Metab. 32(5):954-66, 2007.

Chauvin, et al., "Ribosomal protein S6 kinase activity controls the ribosome biogenesis transcriptional program." Oncogene. vol. 33, 2014, pp. 474-483.

Cheung, et al., "Complete deletion of Apc results in severe polyposis in mice", Oncogene, 29:1857-64, 2010.

Cruzado et al., "Nonimmunosuppressive effects of mammalian target of rapamycin inhibitors," *Transplantation Reviews*, 2007; 21(1): 73-81.

Demetrius, "Aging in Mouse and Human Systems: A Comparative Study," *Acad Sci.*, 2006; 1067:66-82.

Efeyan & Sabatini, "mTOR and cancer: many loops in one pathway", Curr Opin Cell Biol. 22(2):169-76, 2009.

Estep et al., "Short-term calorie restriction in male mice feminizes gene expression and alters key regulators of conserved aging regulatory pathways," PLoS One. 2009;4(4):e5242.

Fajadet et al., "Randomized, double-blind, multicenter study of the Endeavor zotarolimus-eluting phosphorylcholine-encapsulated stent for treatment of native coronary artery lesions. Clinical and angiographic results of the Endeavor II Trial," Minerva Cardioangiol. Feb. 2007;55(1):1-18.

Finkel, et al., "The common biology of cancer and ageing", Nature. 448:767-774, 2007.

Fujishita, et al., "Inhibition of the mTORC1 pathway suppresses intestinal polyp formation and reduces mortality in Apc0716 mice", Proc Natl Acad Sci USA. 105(36):13544-9, 2008.

Ghanbarzadeh, et al., "Improvement of the antiproliferative effect of rapamycin on tumor cell lines by poly (monomethylitaconate)-based pH-sensitive, plasma stable liposomes" Colloids and Surface. 115:323-30, 2014.

Giardiello, et al., "Treatment of colonic and rectal adenomas with sulindac in familial adenomatous polyposis", New England J Med. 328(18):1313-6, 1993.

Graziani, et al., "Recent advances in the chemistry, biosynthesis and pharmacology of rapamycin analogs." Nat Prod Rep. vol. 26, No. 5, 2009, pp. 602-609.

Gregory et al., "Isolation and characterization of pre-rapamycin, the first macrocyclic intermediate in the biosynthesis of the immunosuppressant rapamycin by S. hygroscopicus." Angew Chem Int Ed Engl. vol. 43, No. 19, 2004, pp. 2551-2553.

(56) References Cited

OTHER PUBLICATIONS

Gregory et al., "Rapamycin biosynthesis: Elucidation of gene product function." Org Biomol Chem. vol. 4, No. 19, 2006, pp. 3565-3568.
Guertin and Sabatini, "The pharmacology of mTOR inhibition," *Sci. Signal.*, 2(67):pe24, 2009.
Hansen et al., "Lifespan extension by conditions that inhibit translation in *Caenorhabditis elegans*," Aging Cell, 6:95-110, 2007.
Harrison, et al., "Rapamycin fed late in life extends lifespan in genetically heterogeneous mice", Nature. 460(7253):392-5, 2009.
Hasty, et al., "eRapa Restores a Normal Life Span in a FAP Mouse Model." Cancer Prev Res. 7:169-178, 2014.
Hursting, et al., "Calorie restriction, aging, and cancer prevention: mechanisms of action and applicability to humans." Annu Rev Med. vol. 54, 2003, pp. 131-152.
Inoki et al. "TSC2 Integrates Wnt and Energy Signals via a Coordinated Phosphorylation by AMPK and GSK3 to Regulate Cell Growth" *Cell* 8, 2006, 126, 955-68.
International Preliminary Report on Patentability issued in PCT/US2014/026329, dated Sep. 24, 2015.
International Search Report and Written Opinion issued in PCT/US14/26329, dated Jul. 3, 2014.
Janus, et al., "The mammalian target of the rapamycin (mTOR) kinase pathway: its role in tumourigenesis and targeted antitumor therapy", Cell Mol Biol Lett. 10(3):479-98, 2005.
Jhunjhunwala, et al., "Delivery of Rapacycin to Dendritic Cells Using Degradable Microparticles," J Control Release. 133:191-197, 2009.
Kapahi et al., "Regulation of lifespan in *Drosophila* by modulation of genes in the TOR signaling pathway," *Curr. Biol.*, 14:885-890, 2004.
Kim, et al., "Chemoprevention in familial adenomatous polyposis", Best Pract Res Clin Gastroenterol. 25(4-5):607-22, 2011.
Kinzler, et al., "Identification of FAP locus genes from chromosome 5q21." Science. vol. 253, No. 5020, 1991, pp. 661-665.
Koehl, et al., "Rapamycin inhibits oncogenic intestinal ion channels and neoplasia in APCÔmin/+ mice", Oncogene, 29:1553-60, 2010.
Korinek, et al., "Constitutive transcriptional activation by a beta-catenin-Tcf complex in APC−/− colon carcinoma." Science. vol. 275, 1997, pp. 1784-1787.
Kunstyr, et al., "Gerontological data of C57BL/6J mice. I. Sex differences in survival curves." J Gerontol. vol. 30, No. 2, 1975, pp. 157-162.
Labayle, et al., "Sulindac causes regression of rectal polyps in familial adenomatous polyposis." Gastroenterology. vol. 101, No. 3, 1991, pp. 635-639.
Leung et al., "Challenging the 10-year rule: The accuracy of patient life expectancy predictions by physicians in relation to prostate cancer management," *Can. Urol. Assoc. J.*. 2012; 6(5): 367-73.
Masoro, "Overview of caloric restriction and ageing." Mech Ageing Dev. vol. 126, 2005, pp. 913-922.
Miller et al., "An Aging Interventions Testing Program: study design and interim report," *Aging Cell*, 6:565-575, 2007.
Miller, et al., "Multimodal imaging of growth and rapamycin-induced regression of colonic adenomas in Apc mutation-dependent mouse" Translational Oncol. 5(5):313-20, 2012.
Miller, et al., "Rapamycin, But Not Resveratrol or Simvastatin, Extends Life Span of Genetically Heterogeneous Mice", J Gerontol A Biol Sci Med Sci. 66(2):191-201, 2011.
Morin, et al., "Activation of beta-catenin-Tcf signaling in colon cancer by mutations in beta-catenin or APC." Science. vol. 275, 1997, pp. 1787-1790.
Nadon et al., "Design of aging intervention studies: the NIA interventions testing program," *AGE*, 30(4):187-199, 2008.
Pallet, et al., "Sirolimus early graft nephrotoxicity: clinical and experimental data." Curr Drug Saf. vol. 1, 2006, pp. 179-187.
PCT International Preliminary Report on Patentability issued in International Application No. PCT/US2009/064044, dated May 26, 2011.
PCT International Search Report and Written Opinion issued in International Application No. PCT/US2009/064044, dated Jun. 25, 2010.
Powers III et al., "Extension of chronological life span in yeast by decreased TOR pathway signaling," *Genes & Development*, 20:174-184, 2006.
Rao et al., "Mammalian Target of Rapamycin (mTOR) Inhibitors as Anti-Cancer Agents," *Current Cancer Drug Targets*, 2004; 4(8): 621-635.
Rigau, et al., "Effects of long-term sulindac therapy on colonic polyposis." Ann Int Med. vol. 115, No. 12, 1991, pp. 952-954.
Sankhala, et al., "Review: desmoplastic small round cell tumor: current treatment approach and role of targeted therapy." Clin Adv Hematol Oncol. vol. 7, No. 7, 2009, pp. 476-478.
Schwecke et al., "The biosynthetic gene cluster for the polyketide immunosuppressant rapamycin", Proc Natl Acad Sci USA. 92(17):7839-43, 1995.
Search Report issued in European Application No. 09826677.8, dated May 22, 2012.
Serruys, et al., "Rapamycin eluting stent: the onset of a new era in interventional cardiology", Heart. 87:305-307, 2002.
Shavelle et al., "Rating the Raters: Evaluating the Predictions from a Life Expectancy Rating Service," *J. Insur. Med.*, 2009; 41(3): 178-90.
Shaw et al., "Ras, PI(3)K and mTOR signalling controls tumour cell growth." Nature. vol. 441, 2006, pp. 424-430.
Soerjomataram et al. "Most colorectal cancer survivors live a large proportion of their remaining life in good health," *Cancer Causes Control*, 2012; 23(9): 1421-1428.
Solomon, et al., "Cardiovascular Risk Associated with Celecoxib in a Clinical Trial for Colorectal Adenoma Prevention", New England J Med. 352(11):1071-80, 2005.
Sonenberg & Hinnebusch, "Regulation of Translation Initiation in Euraryotes: Mechanisms and Biological Targets", Cell. 136(4):731-45, 2009.
Steinbach, et al., "The effect of Celecoxib, a cyclooxygenase-2 inhibitor, in familial adenomatous polyposis", New England J Med. 342(26):1946-52, 2000.
Storer, "Longevity and gross pathology at death in 22 inbred mouse strains." J Gerontol. vol. 21, No. 3, 1966, pp. 404-409.
Supplementary Search Report in European Application No. 14772920.6 dated Aug. 1, 2016.
Tabernero et al., "Dose- and Schedule-Dependent Inhibition of the Mammalian Target of Rapamycin Pathway with Everolimus: A Phase I Tumor Pharmacodynamic Study in Patients with Advanced Solid Tumors," *J. of Clinical Oncology*, 2008; 26(10).
Tsang et al., "Targeting mammalian target of rapamycin (mTOR) for health and diseases," *Drug Discovery Today*, 12(3/4):112-124, 2007.
Ulrich, et al., "Skin Cancer in Organ Transplant Recipients—Where Do We Stand Today?", Am J Transplant. 8:2192-8, 2008.
Vasen, et al., "Guidelines for the clinical management of familial adenomatous polyposis (FAP)." Gut. vol. 57, No. 5, 2008, pp. 704-713.
Wallace et al., "Upper gastrointestinal disease in patients with familial adenomatous polyposis." Br J Surg. Vol. 85, No. 6, 1998, pp. 742-750.
Wijnhoven, et al., "Accelerated aging pathology in ad libitum fed Xpd(TTD) mice is accompanied by features suggestive of caloric restriction." DNA Repair (Amst). vol. 4, No. 11, 2005, pp. 1314-1324.
Wislez et al., "Inhibition of Mammalian Target of Rapamycin Reverses Alveolar Epithelial Neoplasia Induced by Oncogenic K-ras," *Cancer Res.*, 2005; 65: 3226.
Yang Wenjun & Wen Longping, "Small Molecule Autophagy Induces," *Progress in Chemistry*, 2007; 19(12): 2013-6.
Yu, et al., "A Retrospective Study of Conversion From Tacrolimus-based to Sirolimus-based Immunosuppression in Orthotopic Liver Transplant Recipients", Exp Clin Transplant. 6:113-7, 2008.
Zell, et al., "Risk of Cardiovascular Events in a Randomized Placebo-Controlled, Double-Blind Trial of Difluoromethylornithine Plus Sulindac for the Prevention of Sporadic Colorectal Adenomas", Cancer Prev Res. 2(3):209-12, 2009.

(56) References Cited

OTHER PUBLICATIONS

Zoncu, et al., "mTOR: from growth signal integration to cancer, diabetes and ageing", Nat Rev Mol Cell Biol. 12:21-35, 2010.

* cited by examiner

FYI : Approx. Number of Rapamycin Molecules in a Nanoparticle can be Estimated as Follows:

$$N_R \approx \frac{1.18 \times 602 \times \pi \times D^3}{914.2 \times 6}$$ e.g. D = 230nm, then $N_R$ = 4.9 × $10^6$, or about 5 million molecules

USE OF MTOR INHIBITORS FOR TREATMENT OF FAMILIAL ADENOMATOUS POLYPOSIS

PRIORITY CLAIM

This application is a continuation from U.S. application Ser. No. 15/337,410, filed Oct. 28, 2016, which is a continuation from U.S. application Ser. No. 14/775,291 filed Sep. 11, 2015, which is an application under 35 USC 371 from PCT/US2014/026329 filed Mar. 13, 2014, which claims the benefit of priority to U.S. Application No. 61/778,670, filed Mar. 13, 2013, all of which are hereby incorporated by reference in their entirety.

GOVERNMENTAL RIGHTS

This invention was made with government support under agreement number AG036613 awarded by the National Institutes of Health (NIH). The government has certain rights in the invention.

BACKGROUND OF THE INVENTION

A. Field of the Invention

The invention relates to methods and compositions for treating or preventing intestinal adenomas or polyps or preventing cancer in a patient who has been identified as being at risk for developing intestinal polyps or intestinal cancer. The methods and compositions include rapamycin, rapamycin analogs, or other inhibitors of the mammalian target of rapamycin ("mTOR" or "mTORC1").

B. Description of Related Art

Intestinal cancer encompasses a variety of cancers, including cancer of the small intestine, gastric cancer, and colorectal cancer. Historically, the most common treatment of intestinal cancer is surgery and radiation therapy. To date, there are no effective therapies for prevention of intestinal cancers. Rather, most treatments focus on early detection and treatment of existing cancers.

There are three main roles that chemoprevention can play in colorectal cancer (CRC) patients: (1) to delay prophylactic colectomy; (2) to prevent cancer development in the retained rectum in patients after colectomy with ileorectal anastomosis (IRA); and (3) to prevent cancer development in the upper gastrointestinal tract, especially the duodenum. Nonsteroidal anti-inflammatory drugs (NSAIDs) including sulindac and celecoxib, ursodeoxycholic acid, statins, difluoromethylornithine (DFMO), and various dietary supplements have been studied as potential chemopreventive agents (Kim 2011). The non-selective, non-steroidal anti-inflammatory drug (NSAID) sulindac can be given to delay the progression of polyposis in the retained rectum among patients after colectomy with IRA but should be used in conjunction with a strict endoscopic surveillance regimen (Giardiello 1993; Labayle 1991; Rigau 1991). In a 6-month trial in adults with FAP, the selective cyclooxygenase inhibitor celecoxib was found to be well tolerated and significantly reduced colorectal adenomas (Steinbach 2000). Sulindac or celecoxib is not recommended as a primary chemopreventive agent. Despite apparent effectiveness, reports of potential cardiovascular toxicity with COX-2 inhibitors limit their use in FAP (Solomon 2005).

The benefit of regular use of COX-2 inhibitors and non-selective NSAIDs in FAP patients with cardiovascular risk factors needs to be weighed against the potential cardiovascular adverse events of these medications. Cardiovascular complications do not appear to be limited to COX-2 inhibitor use. Non-selective NSAIDs, including sulindac and naproxen, have been suggested to increase cardiovascular thrombotic events (Zell 2009). Chemoprevention should ideally be well tolerated, low in toxicity, inexpensive, and effective for long-term use.

In view of this, there remains a need for therapies that prevent intestinal cancer and treat underlying symptoms that lead to cancer.

SUMMARY OF THE INVENTION

In some aspects, provided are methods for preventing intestinal polyps or intestinal cancer in a patient comprising administering an effective amount of a composition comprising rapamycin or an analog thereof to a patient who has been identified as being at risk for developing intestinal polyps or intestinal cancer.

In some embodiments, the patient has been identified as being at risk for developing intestinal polyps or intestinal cancer. In some embodiments, this risk is identified on the basis of disease state, prior diagnosis, family history, diet, age, or other factors. In some embodiments, the patient has been diagnosed with an inflammatory bowel disease. In some embodiments, the patient has been diagnosed with an intestinal polyp or an adenoma. In some embodiments, the patient has been diagnosed as having a mutation that is known to cause increased WNT signaling. In some embodiments, the patient has been diagnosed as having Familial Adenomatous Polyposis (FAP). In some embodiments, the patient has a family history of intestinal polyps or intestinal cancer. In some embodiments, the patient is between the ages of 1 to 18 years, 18 years to 50 years, or over the age of 50 years.

In some embodiments, the rapamycin or analog thereof is encapsulated or coated, or the composition comprising the rapamycin or analog thereof is encapsulated or coated. In some embodiments, the encapsulant or coating may be an enteric coating. In some embodiments, the encapsulant or coating may be an enteric coating. In some embodiments, the coating comprises cellulose acetate succinate, hydroxy propyl methyl cellulose phthalate co-polymer, or a polymethacrylate-based copolymer selected from the group consisting of methyl acrylate-methacrylic acid copolymer, and a methyl methacrylate-methacrylic acid copolymer. In some embodiments, the coating comprises Poly(methacylic acid-co-ethyl acrylate) in a 1:1 ratio, Poly(methacrylic acid-co-ethyl acrylate) in a 1:1 ratio, Poly(methacylic acid-co-methyl methacrylate) in a 1:1 ratio, Poly(methacylic acid-co-methyl methacrylate) in a 1:2 ratio, Poly(methyl acrylate-co-methyl methacrylate-co-methacrylic acid) in a 7:3:1 ratio, Poly(ethyl acrylate-co-methyl methacrylate-co-trimethylammonioethyl methacrylate chloride) in a 1:2:0.2 ratio, Poly(ethyl acrylate-co-methyl methacrylate-co-trimethylammonioethyl methacrylate chloride) in a 1:2:0.1 ratio, or Poly(butyl methacrylate-co-(2-dimethylaminoethyl) methacrylate-co-methyl methacrylate) in a 1:2:1 ratio, a naturally-derived polymer, or a synthetic polymer, or any combination thereof. In some embodiments, the naturally-derived polymer is selected from the group consisting of alginates and their various derivatives, chitosans and their various derivatives, carrageenans and their various analogues, celluloses, gums, gelatins, pectins, and gellans. In some embodiments, the naturally-derived polymer is selected from the group consisting of polyethyleneglycols (PEGs) and polyethyleneoxides (PEOs), acrylic acid homo- and copolymers with acrylates and methacrylates, homopolymers of acrylates and methacrylates, polyvinyl alcohol PVOH), and polyvinyl pyrrolidone (PVP).

An effective amount of rapamycin or rapamycin analog or derivative will depend upon the disease to be treated, the length of duration desired and the bioavailability profile of the implant, and the site of administration. In some embodiments, the composition comprises rapamycin or an analog thereof at a concentration of 0.001 mg to 30 mg total per dose. In some embodiments, the composition comprising rapamycin or an analog of rapamycin comprises 0.001% to 60% by weight of rapamycin or an analog of rapamycin. In some embodiments, the average blood level of rapamycin in the subject is greater than 0.5 ng per mL whole blood after administration of the composition.

The composition can be administered to the subject using any method known to those of ordinary skill in the art. In some embodiments, the composition may be administered intravenously, intracerebrally, intracranially, intraventricularly, intrathecally, into the cortex, thalamus, hypothalamus, hippocampus, basal ganglia, substantia nigra or the region of the substantia nigra, cerebellum, intradermally, intraarterially, intraperitoneally, intralesionally, intratracheally, intranasally, topically, intramuscularly, intraperitoneally, anally, subcutaneously, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other methods or any combination of the forgoing as would be known to one of ordinary skill in the art. In some embodiments, the composition is administered orally, enterically, colonically, anally, intravenously, or dermally with a patch. In some embodiments, the composition comprising rapamycin or an analog of rapamycin is comprised in a food or food additive.

The dose can be repeated as needed as determined by those of ordinary skill in the art. In some embodiments, the rapamycin or analog of rapamycin is administered in two or more doses. Where more than one dose is administered to a subject, the time interval between doses can be any time interval as determined by those of ordinary skill in the art. For example, the two doses may be 1, 2, 3, 4, 5, 6, 7, 8, 9, 10, 11, 12, 13, 14, 15, 16, 17, 18, 29, 20, 21, 22, 23, or 24 hours apart, or any range therein. In some embodiments, the composition may be administered daily, weekly, monthly, annually, or any range therein. In some embodiments, the interval of time between administration of doses comprising rapamycin or an analog of rapamycin is between 0.5 to 30 days.

In some embodiments, the method comprises further administering one or more secondary or additional forms of therapies. In some embodiments, the subject is further administered a composition comprising a second active agent. In some embodiments, the second active agent is metformin, celecoxib, eflornithine, sulindac, ursodeoxycholic acid, an anti-inflammatory agent, an anti-autoimmune agent, or a cytotoxic or cytostatic anti-cancer agent. In some embodiments, the composition comprising rapamycin or an analog of rapamycin is administered at the same time as the composition comprising the second active agent. In some embodiments, the composition comprising rapamycin or an analog of rapamycin is administered before or after the composition comprising the second active agent is administered. In some embodiments, the two treatments may be 1, 2, 3, 4, 5, 6, 7, 8, 9, 10, 11, 12, 13, 14, 15, 16, 17, 18, 29, 20, 21, 22, 23, or 24 hours apart, 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, or 31 days apart, 1, 2, 3, 4, 5, 6, 7, 8, 9, 10, 11, or 12 months apart, or one or more years apart or any range therein. In some embodiments, the interval of time between administration of composition comprising rapamycin or an analog of rapamycin and the composition comprising the second active agent is 1 to 30 days.

In some embodiments, the composition comprising rapamycin or an analog of rapamycin prevents intestinal polyps or intestinal cancer. In some embodiments, the composition comprising rapamycin or an analog of rapamycin prevents the development of new adenomas or polyps, decreases the number or severity of the adenomatous polyps, induces a reduction in size or number of existing adenomas or polyps, prevents the conversion of adenomas or polyps into adenocarcinomas and cancer tissue, or prevents the adenomas or polyps from converting into malignant cancer that spread into other bodily tissues, organs and blood systems in a patient that has been diagnosed as having intestinal adenomas, intestinal polyps or Familial Adenomatous Polyposis (FAP).

In some embodiments, the mTOR inhibitor or an analog thereof is eRapa. "eRapa" is generically used to refer to encapsulated or coated forms of Rapamycin or other mTOR inhibitors or their respective analogs disclosed herein and equivalents thereof. In some embodiments, the encapsulant or coating used for and incorporated in eRapa preparation may be an enteric coating. In some embodiments, the mTOR inhibitor or analog thereof is nanoRapa. "nanoRapa" is generically used to refer to the rapamycins, rapamycin analogs, or related compositions within the eRapa preparation are provided in the form of nanoparticles that include the rapamycin or other mTOR inhibitor. In some embodiments, the mTOR inhibitor or analog thereof is e-nanoRapa. "e-nanoRapa" is generically used to refer to eRapa variations formed from nanoRapa particles. After preparing the nanoRapa preparations, the nanoRapa preparation may then be coated with an enteric coating, to provide an eRapa preparation formed from nanoRapa particles.

In some embodiments, the eRapa, nanoRapa, or e-nanoRapa is encased in a coating comprising cellulose acetate succinate, hydroxy propyl methyl cellulose phthalate copolymer, or a polymethacrylate-based copolymer selected from the group consisting of methyl acrylate-methacrylic acid copolymer, and a methyl methacrylate-methacrylic acid copolymer. In some embodiments, the coating comprises Poly(methacylic acid-co-ethyl acrylate) in a 1:1 ratio, Poly(methacrylic acid-co-ethyl acrylate) in a 1:1 ratio, Poly(methacylic acid-co-methyl methacrylate) in a 1:1 ratio, Poly(methacylic acid-co-methyl methacrylate) in a 1:2 ratio, Poly(methyl acrylate-co-methyl methacrylate-co-methacrylic acid) in a 7:3:1 ratio, Poly(ethyl acrylate-co-methyl methacrylate-co-trimethylammonioethyl methacrylate chloride) in a 1:2:0.2 ratio, Poly(ethyl acrylate-co-methyl methacrylate-co-trimethylammonioethyl methacrylate chloride) in a 1:2:0.1 ratio, or Poly(butyl methacylate-co-(2-dimethylaminoethyl) methacrylate-co-methyl methacrylate) in a 1:2:1 ratio, a naturally-derived polymer, or a synthetic polymer, or any combination thereof. In some embodiments, the naturally-derived polymer is selected from the group consisting of alginates and their various derivatives, chitosans and their various derivatives, carrageenans and their various analogues, celluloses, gums, gelatins, pectins, and gellans. In some embodiments, the naturally-derived polymer is selected from the group consisting of polyethyleneglycols (PEGs) and polyethyleneoxides (PEOs), acrylic acid homo- and copolymers with acrylates and methacrylates, homopolymers of acrylates and methacrylates, polyvinyl alcohol PVOH), and polyvinyl pyrrolidone (PVP).

In some embodiments, the composition comprises eRapa or an analog thereof at a concentration of at or between 50 micrograms and 200 micrograms per kilogram for daily administration, or the equivalent for other frequencies of administration.

In some embodiments, the eRapa, nanoRapa, or e-nanoRapa is administered orally, enterically, colonically, anally, intravenously, or dermally with a patch. In some embodiments, the eRapa, nanoRapa, or e-nanoRapa is administered in two or more doses. In some embodiments, the interval of time between administration of doses comprising eRapa, nanoRapa, or e-nanoRapa is 0.5 to 30 days. In some embodiments, the interval of time between administration of doses comprising eRapa, nanoRapa, or e-nanoRapa is 0.5 to 1 day. In some embodiments, the interval of time between administration of doses comprising eRapa, nanoRapa, or e-nanoRapa is 1 to 3 days. In some embodiments, the interval of time between administration of doses comprising eRapa, nanoRapa, or e-nanoRapa is 1 to 5 days. In some embodiments, the interval of time between administration of doses comprising eRapa, nanoRapa, or e-nanoRapa is 1 to 7 days. In some embodiments, the interval of time between administration of doses comprising eRapa, nanoRapa, or e-nanoRapa is 1 to 15 days.

In some embodiments, the subject is further administered a composition comprising a second active agent. In some embodiments, the second active agent is metformin, celecoxib, eflornithine, sulindac, ursodeoxycholic acid, an anti-inflammatory agent, an anti-autoimmune agent, or a cytotoxic or cytostatic anti-cancer agent. In some embodiments, the composition comprising eRapa, nanoRapa, or e-nanoRapa is administered at the same time as the composition comprising the second active agent. In some embodiments, the composition comprising eRapa, nanoRapa, or e-nanoRapa is administered before or after the composition comprising the second active agent is administered. In some embodiments, the interval of time between administration of composition comprising eRapa, nanoRapa, or e-nanoRapa and the composition comprising the second active agent is 1 to 30 days.

In some embodiments, the composition comprising eRapa, nanoRapa, or e-nanoRapa prevents intestinal polyps or intestinal cancer. In some embodiments, the composition comprising eRapa, nanoRapa, or e-nanoRapa prevents the development of new adenomas or polyps, decreases the number or severity of the adenomatous polyps, induces a reduction in size or number of existing adenomas or polyps, prevents the conversion of adenomas or polyps into adenocarcinomas and cancer tissue, or prevents the adenomas or polyps from converting into malignant cancer that spread into other bodily tissues, organs and blood systems in a patient that has been diagnosed as having intestinal adenomas, intestinal polyps or Familial Adenomatous Polyposis (FAP).

In some embodiments, the composition comprising eRapa, nanoRapa, or e-nanoRapa is comprised in a food or food additive.

Unless otherwise specified, the percent values expressed herein are weight by weight and are in relation to the total composition.

The term "about" or "approximately" is defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result. Similarly, the term "effective" means adequate to accomplish a desired, expected, or intended result.

The terms "prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. in relation to the total composition.

The compositions and methods for their use can "comprise," "consist essentially of," or "consist of" any of the ingredients or steps disclosed throughout the specification. With respect to the transitional phrase "consisting essentially of," in one non-limiting aspect, a basic and novel characteristic of the compositions and methods is the ability of eRapa, e-nanoRapa or other rapamycin preparations to treat or prevent intestinal polyps or prevent cancer in a patient who has been identified as being at risk for developing intestinal polyps or intestinal cancer, most especially in subjects who are suspected or known to have a genetic predisposition for developing familial adenomatous polyposis (FAP).

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The inventors have discovered an effective therapy for treating or preventing intestinal polyps or preventing cancer in a patient who has been identified as being at risk for developing intestinal polyps or intestinal cancer comprising administration of rapamycin, an analog of rapamycin, or another inhibitor of mTOR. In certain embodiments, the rapamycin, an analog of rapamycin, or other inhibitor of mTOR is administered orally. In certain embodiments, the rapamycin, an analog of rapamycin, or other inhibitor of mTOR is administered in the form of an eRapa and/or e-nanoRapa preparation.

Figures 2A, 2B, 2C:
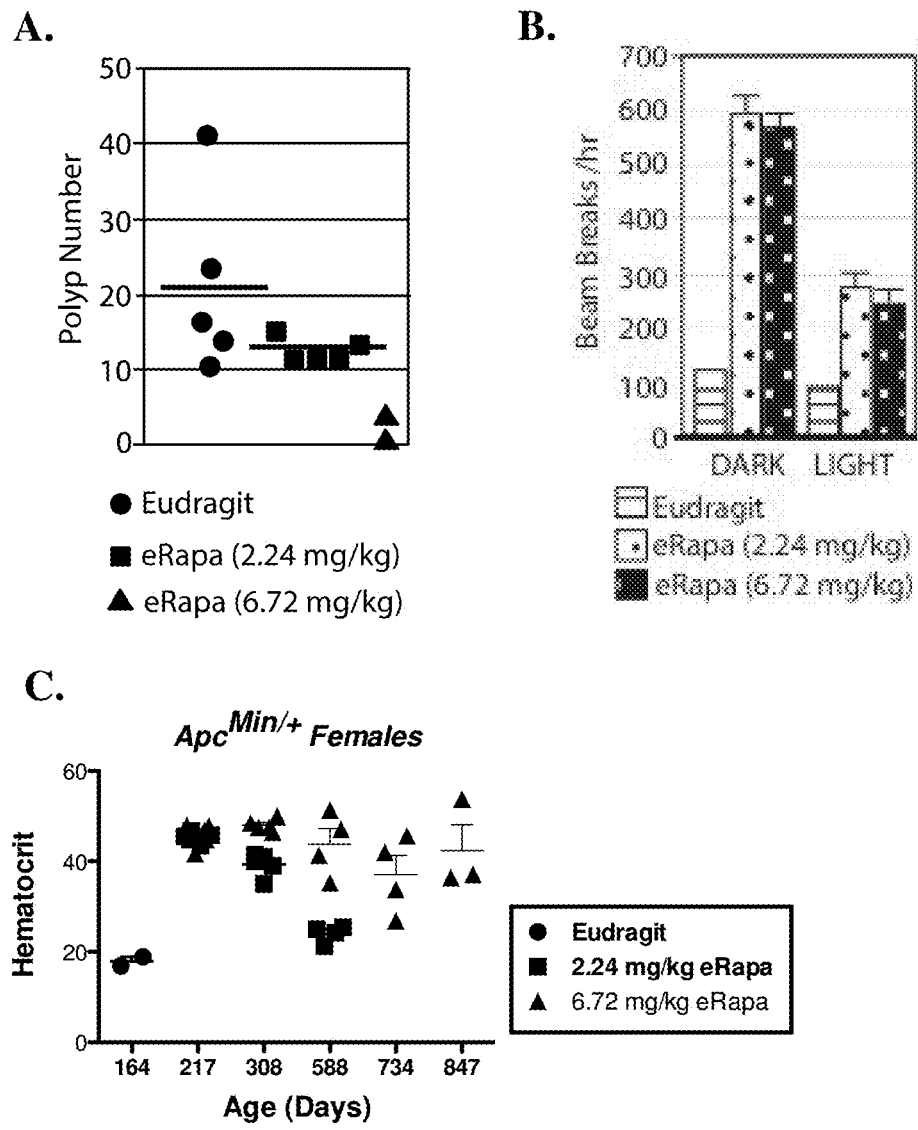
FIGS. 2A-2C (A) Polyp count in Apc$^{Min/+}$ mice at time of death in mice treated with no eRapa (left cluster, solid circles), the medium dose of eRapa as described above (middle cluster, solid squares), or the high dose of eRapa as described above (right cluster, solid triangles). (B) Encapsulated Rapa improves physical activity in Apc$^{Min/+}$ mice, as shown by measuring the average number of beam breaks (activity) for two time periods of the day, light and dark. Mice were treated with Eudragit control diet (left column, hatched), the medium dose of eRapa as described above (middle column, white with black dots), or the high dose of eRapa as described above (right column, black with white dots) The food area of the cage was excluded. (C) Encapsulated Rapa maintains normal hematocrits in Apc$^{Min/+}$ mice. Mice were treated with no eRapa (solid black circles), the medium dose of eRapa (solid black squares), or the high dose of eRapa (solid black triangles). Age at the time of hematocrits is indicated on the X-axis.
Figures 3A, 3B, 3C:
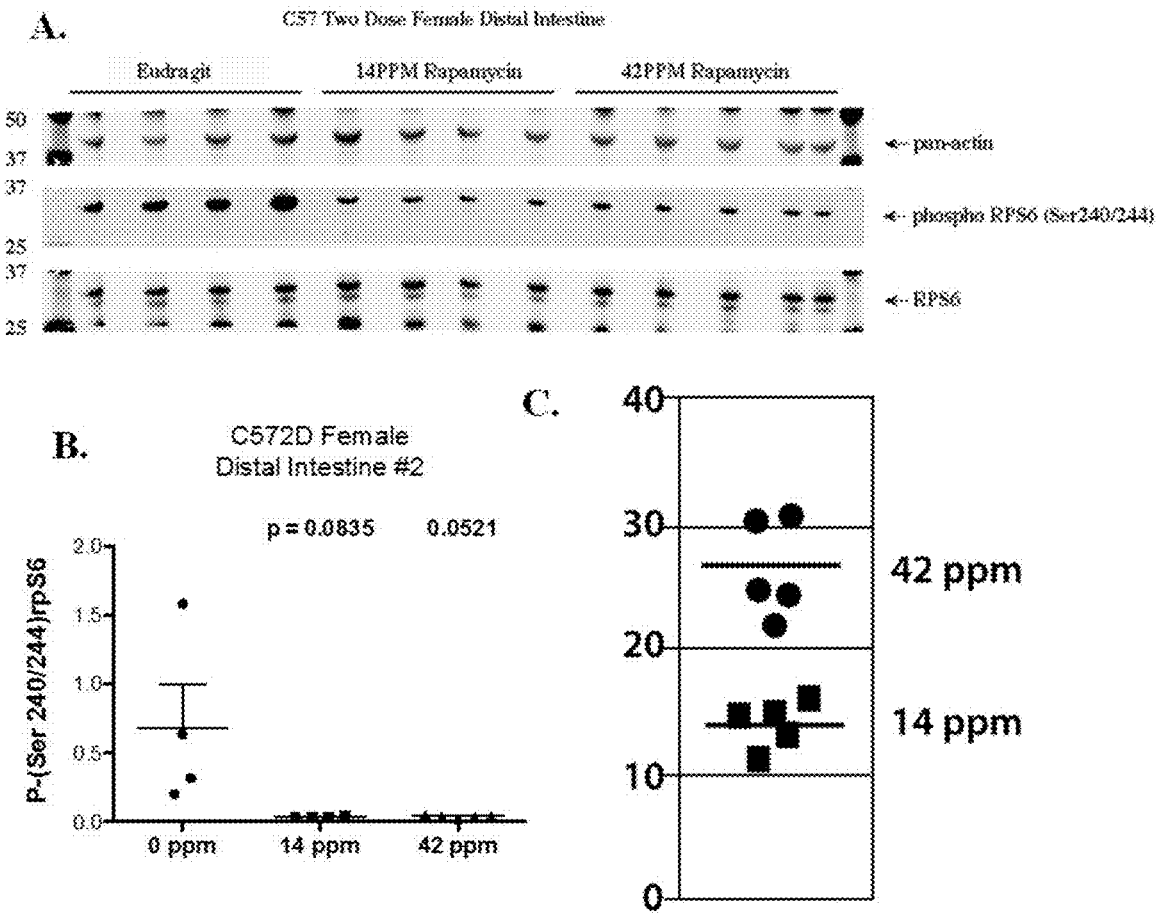
FIGS. 3A-3C. Encapsulated Rapamycin inhibits mTOR complex 1 (mTORC1) downstream effector, ribosomal protein subunit S6 (rpS6) phosphorylation by S6 kinase 1 (S6K1) in the distal segment of small intestine. eRapa was fed to C57BL/6 mice, the same genetic background for the Apc$^{Min/+}$, and intestines were collected and prepared for immunoassay. (A) Immunoblot showing detection of total rpS6 (bottom panel), Ser240/244 phosphorylated rpS6 (middle panel) and pan actin as a loading control. (B) Signal intensities for each band in (A) were quantified and the ratio of phosphorylated rpS6 to total rpS6 was calculated and graphed as a scatter plot using Prism Software. Statistical significance of the reduction in this ratio was determined using an un-paired t-test (Prism). These data show that eRapa effectively inhibited, mTORC1 and its effector rpS6, which is known to play a vital role in biogenesis of ribosomes used in protein synthesis needed for cell growth and proliferation. This is likely the effect of eRapa that inhibits polyp development and growth in Apc$^{Min/+}$ mice and extends longevity. (C) Blood levels of rapamycin at 217 days (174 days treatment with eRapa) in mice treated with 14 ppm eRapa (the medium dose of eRapa as described above, see bottom cluster, shown in solid black squares) and 42 ppm eRapa (the high dose of eRapa as described above, see top cluster, shown in solid black circles).

Chemoprevention should ideally be well tolerated, low in toxicity, inexpensive, and effective for long-term use; therefore, the compositions disclosed herein appear to be ideal for this purpose. As shown in FIG. 1-2, encapsulated rapamycin demonstrates significant potential in preventing, delaying and/or reducing the severity of intestinal polyps, as evidenced by prevention of anemia (FIG. 2C, 3C).

A. Intestinal Cancer

Intestinal cancer encompasses a variety of cancers, including cancer of the small intestine, gastric cancer, and colorectal cancer. Symptoms of intestinal cancer often include, but are not limited to, pain throughout the body, unexplained weight-loss, pain or cramping in the middle of the abdomen, a lump in the abdomen, blood in the stool, nausea, bloating, iron deficient anemia, and jaundice. Historically, the most common treatment of intestinal cancer is surgery and radiation therapy.

Intestinal cancer is more likely to occur in some patients than others. For example, intestinal cancer is more likely to occur in a patient that has been diagnosed with an inflammatory bowel disease, an intestinal polyp or an adenoma, Familial adenomatous polyposis (FAP), or as having a mutation which is known to cause increased WNT signaling. In other embodiments, the patient has a family history of intestinal polyps or intestinal cancer.

Small intestine cancer can be further divided into a variety of subtypes, including cancer of the jejunum and ileum, duodenal cancer, adenocarcinoma, gastrointestinal stromal tumors, lymphoma, and ileal carcinoid tumors. Adenocarcinoma is a type of cancer that begins in the lining of the small intestine, and make up 40-50% of all small intestinal cancers. This type of intestinal cancer occurs most often later in life. People with Crohn's Disease and certain other inherited conditions such as familial adenomatous polyposis and Peuts-Jegherssyndrome are at a higher risk of developing adenocarcinomas. Carcinoid tumors occur when neuroendocrine cells grow abnormally, and may also be referred to as neuroendocrine tumors or neuroendocrine cancer. People with a family history of multiple endocrine neoplasia or a family history of neurofibromatosis are more likely to get carcinoid tumors. Carcinoid tumors are also more common in women, African Americans, and people with certain diseases that damage the stomach and reduce the amount of stomach acid. Gastrointestinal stromal tumors start in the interstitial cells of Cajal (ICCs) in the walls of the GI tract. It is believed that a family history of neurofibromatosis or familial gastrointestinal stromal tumor syndrome will increase a patient's risk of getting stromal tumors. Gastrointestinal lymphomas are a cancer of the lymphatic system that begins in the lymphoid tissue. It is believed that old age, genetic risk factors that cause abnormal function of the immune system, a diet high in animal fat and low in fruits and vegetables, exposure to radiation and certain chemicals, immune deficiencies, and some infections increase the likelihood of a lymphoma developing.

Colorectal cancer, commonly also known as colon cancer or bowel cancer, is a cancer from uncontrolled cell growth in the colon, rectum, or appendix. The majority of colorectal cancers are due to lifestyle and increasing age, but some are associated with an underlying genetic disorder. For example, people with inflammatory bowel disease (ulcerative colitis and Crohn's disease) are at increased risk of colon cancer. Those with a family history of colorectal cancer in two or more first-degree relatives have a two to threefold greater risk of disease, and a number of genetic syndromes are also associated with higher rates of colorectal cancer. The most common of these is hereditary nonpolyposis colorectal cancer (HNPCC or Lynch syndrome) which is present in about 3% of people with colorectal cancer. Other syndromes that are strongly associated include: Gardner syndrome, and familial adenomatous polyposis (FAP).

Gastric cancer refers to cancer arising from any part of the stomach, and is often either asymptomatic or causes only nonspecific symptoms in its early stages. Infection by *Helicobacter pylori* is believed to be the cause of most stomach cancer while autoimmune atrophic gastritis, intestinal metaplasia, and various genetic factors are associated with increased risk levels. A very important but preventable cause of gastric cancer is tobacco smoking. Gastric cancers due to smoking mostly occur in the upper part of the stomach near the esophagus.

B. Familial Adenomatous Polyposis (FAP)

Familial adenomatous polyposis (FAP) is an autosomal dominant disease caused by mutation of the Adenomatous Polyposis *Coli* (APC) gene, located on chromosome 5 (Kinzler 1991). This germline defect accelerates the initiation of the adenoma-carcinoma, resulting in the development of numerous adenomatous colorectal polyps at a young age. Polyposis inevitably progresses to colorectal cancer if left untreated. Given the predictable development of colorectal cancer in patients with FAP, the safest preventative strategy is surgical resection of the colon when polyposis develops. The two main prophylactic surgeries are colectomy with ileorectal anastomosis (IRA) and proctocolectomy with ileal pouch-anal anastomosis (IPAA) (Vasen 2008). Genetic screening and endoscopy in concert with prophylactic surgery significantly improved the overall survival of FAP patients. A pharmacological prophylactic approach to prevent these outcomes for this population of patients is obviously in great need.

However, less well appreciated is the second leading cause of death in FAP, duodenal adenocarcinoma. Nearly 90% of patients with FAP develop duodenal polyps, the precursor lesions of duodenal adenocarcinoma and 4.5% will develop duodenal adenocarcinoma in their lifetime (Wallace 1998; Bulow 2004). In contrast to the colon, prophylactic surgical resection of the ampulla and/or duodenum is accompanied by significant morbidity. Duodenal surgery is currently indicated for patients with severe duodenal polyposis or duodenal carcinoma. This patient population has a strong need for adjuvant therapies to surgery to prevent or reduce the polyp formation and carcinogenesis in the gastro-intestinal track.

C. WNT Signaling Pathway

WNTs comprise a family of 19 secreted glycoproteins, which function in diverse biological processes such as cell proliferation, survival and segment polarity during development (Anastas 2013). WNTs signal via transmembrane receptors included in 10 members of the frizzled (FZD) family of G-protein coupled receptors and receptor tyrosine kinases. The first WNT gene was identified in cancer arising in mouse models of mammary cancer and in mouse and human colon cancer. WNTs promote stabilization of a transcription factor called β-catenin (also known as CTNNB1). WNTs control both the canonical β-catenin-dependent and non-canonical (β-catenin-independent pathways. Studies point to a vital role for hyper-activated WNT-β-catenin signaling in colorectal cancer (Korinek 1997; Morin 1997). Inherited inactivating mutations of the adenomatous polyposis coli (APC) gene, the product of which is a negative controller of β-catenin stability, are found in patients with familial adenomatous polyposis (FAP). Polyps of FAP patients progress to colorectal carcinomas upon inactivation of the tumor suppressor p53 and activating mutations of KRAS. Both APC and CTNNB1 are commonly mutated in colorectal cancers of non-FAP patients.

The high prevalence of WNT pathway mutations in many types of cancer is evidence for the importance of the WNT-β-catenin pathway in carcinogenesis. Mutations in other members of the WNT signal pathway implicated in carcinogenesis include: TCF7L2 (transcription factor 7-like), CTNNB1, WTX (Wilms tumor gene on the X chromosome), and AXIN (See Table 1 of Anastas 2013).

D. mTOR Inhibitors and Rapamycin

Any inhibitor of mTORC1 is contemplated for inclusion in the present compositions and methods. In particular embodiments, the inhibitor of mTORC1 is rapamycin or an analog of rapamycin. In some embodiments, the inhibitor of mTORC1 is rapamycin or an analog of rapamycin is administered orally in the form of an eRapa and/or e-nanoRapa preparation. Rapamycin (also known as sirolimus and marketed under the trade name Rapamune) is a known macrolide. The molecular formula of rapamycin is $C_{51}H_{79}NO_{13}$.

Rapamycin binds to a member of the FK binding protein (FKBP) family, FKBP 12. The rapamycin/FKBP 12 complex binds to the protein kinase mTOR to block the activity of signal transduction pathways. Because the mTOR signaling network includes multiple tumor suppressor genes, including PTEN, LKB1, TSC1, and TSC2, and multiple proto-oncogenes including PI3K, Akt, and eEF4E, mTOR signaling plays a central role in cell survival and proliferation. Binding of the rapamycin/FKBP complex to mTOR causes arrest of the cell cycle in the G1 phase (Janus 2005).

mTORC1 inhibitors also include rapamycin analogs. Many rapamycin analogs are known in the art. Non-limiting examples of analogs of rapamycin include, but are not limited to, everolimus, tacrolimus, CCI-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, and 42-O-(2-hydroxy)ethyl rapamycin.

Other analogs of rapamycin include: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440, 990); water soluble rapamycin esters (U.S. Pat. No. 5,955, 457); alkylated rapamycin derivatives (U.S. Pat. No. 5,922, 730); rapamycin amidino carbamates (U.S. Pat. No. 5,637, 590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carbalkoxy)sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No.

5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842).

Other analogs of rapamycin include those described in U.S. Pat. Nos. 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; 5,023,262; all of which are incorporated herein by reference. Additional rapamycin analogs and derivatives can be found in the following U.S. Patent Application Pub. Nos., all of which are herein specifically incorporated by reference: 20080249123, 20080188511; 20080182867; 20080091008; 20080085880; 20080069797; 20070280992; 20070225313; 20070203172; 20070203171; 20070203170; 20070203169; 20070203168; 20070142423; 20060264453; and 20040010002.

Rapamycin or a rapamycin analog can be obtained from any source known to those of ordinary skill in the art. The source may be a commercial source, or natural source. Rapamycin or a rapamycin analog may be chemically synthesized using any technique known to those of ordinary skill in the art. Non-limiting examples of information concerning rapamycin synthesis can be found in Schwecke et al., 1995; Gregory et al., 2004; Gregory et al., 2006; Graziani, 2009.

E. Encapsulated Rapamycin Compositions

In some aspects, the compositions comprising an inhibitor of mTOR are encapsulated or coated to provide eRapa preparations. In some embodiments, the encapsulant or coating may be an enteric coating. In some embodiments, the compositions comprising an inhibitor of mTOR are provided in the form of nanoRapa nanoparticles, and such nanoRapa nanoparticles are encapsulated or coated to provide e-nanoRapa preparations, which are relatively stable and beneficial for oral administration.

Many pharmaceutical dosage forms irritate the stomach due to their chemical properties or are degraded by stomach acid through the action of enzymes, thus becoming less effective. The coating may be an enteric coating, a coating that prevents release and absorption of active ingredients until they reach the intestine. "Enteric" refers to the small intestine, and therefore enteric coatings facilitate delivery of agents to the small intestine. Some enteric coatings facilitate delivery of agents to the colon. In some embodiments, the enteric coating is a EUDRAGIT (®) coating. Eudragit coatings include Eudragit L100-55 (for delivery to the duodenum), Poly(methacylic acid-co-ethyl acrylate) 1:1; Eudragit L 30 D-55 (for delivery to the duodenum), Poly (methacrylic acid-co-ethyl acrylate) 1:1; Eudragit L 100 (for delivery to the jejunum), Poly(methacylic acid-co-methyl methacrylate) 1:1; Eudragit S100 (for delivery to the ileum), Poly(methacylic acid-co-methyl methacrylate) 1:2; Eudragit FS 30D (for colon delivery), Poly(methyl acrylate-co-methyl methacrylate-co-methacrylic acid) 7:3:1; Eudragit RL (for sustained release), Poly(ethyl acrylate-co-methyl methacrylate-co-trimethylammonioethyl methacrylate chloride) 1:2:0.2; Eudragit RS (for sustained release), Poly(ethyl acrylate-co-methyl methacrylate-co-trimethylammonioethyl methacrylate chloride) 1:2:0.1; and Eudragit E (for taste masking), Poly(butyl methacylate-co-(2-dimethylaminoethyl) methacrylate-co-methyl methacrylate) 1:2:1. Other coatings include Eudragit RS, Eudragit RL, ethylcellulose, and polyvinyl acetate. Benefits include pH-dependent drug release, protection of active agents sensitive to gastric fluid, protection of gastric mucosa from active agents, increase in drug effectiveness, good storage stability, and GI and colon targeting, which minimizes risks associated with negative systemic effects.

Some examples of enteric coating components include cellulose acetate phthalate, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, and stearic acid. The coating may include suitable hydrophilic gelling polymers including but not limited to cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, natural and synthetic gums, such as guar gum, arabic gum, xanthan gum, gelatin, collagen, proteins, polysaccharides, such as pectin, pectic acid, alginic acid, sodium alginate, polyaminoacids, polyalcohols, polyglycols; and the like; and mixtures thereof. Any other coating agent known to those of ordinary skill in the art is contemplated for inclusion in the coatings of the microcapsules set forth herein.

The coating may optionally comprises a plastisizer, such as dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof. The coating may optionally include a gum. Non-limiting examples of gums include homopolysaccharides such as locust bean gum, galactans, mannans, vegetable gums such as alginates, gum karaya, pectin, agar, tragacanth, acacia, carrageenan, tragacanth, chitosan, agar, alginic acid, other polysaccharide gums (e.g., hydrocolloids), acacia *catechu*, salai guggal, indian bodellum, copaiba gum, asafetida, cambi gum, Enterolobium cyclocarpum, mastic gum, benzoin gum, sandarac, gambier gum, butea frondosa (Flame of Forest Gum), myrrh, konjak mannan, guar gum, welan gum, gellan gum, tara gum, locust bean gum, carageenan gum, glucomannan, galactan gum, sodium alginate, tragacanth, chitosan, xanthan gum, deacetylated xanthan gum, pectin, sodium polypectate, gluten, karaya gum, tamarind gum, ghatti gum, Accaroid/ Yacca/Red gum, dammar gum, juniper gum, ester gum, ipil-ipil seed gum, gum talha (acacia seyal), and cultured plant cell gums including those of the plants of the genera: acacia, actinidia, aptenia, carbobrotus, chickorium, cucumis, glycine, hibiscus, hordeum, letuca, lycopersicon, malus, medicago, mesembryanthemum, oryza, panicum, phalaris, phleum, poliathus, polycarbophil, sida, solanum, trifolium, trigonella, Afzelia africana seed gum, Treculia africana gum, detarium gum, cassia gum, carob gum, Prosopis africana gum, Colocassia esulenta gum, Hakea gibbosa gum, khaya gum, scleroglucan, zea, mixtures of any of the foregoing, and the like.

In some aspects, the compositions comprising an inhibitor of mTOR are formed into nanoparticles and subsequently encapsulated or coated. In some embodiments, the encapsulant or coating may be an enteric coating. In some embodiments, the encapsulated rapamycin nanoparticles provide rapamycin nanoparticles within a protective polymer matrix for oral administration of rapamycin. The result is not only more durable and stable, but is also more bioavailable and efficacious for treatment and prevention of genetically-predisposed disorders and age-related disorders, especially in the fields of oncology and neurology in humans and other animals.

The encapsulated rapamycin nanoparticles provide an embodiment of the present invention in the form of an improved form of encapsulated rapamycin that is more durable, stable and bioavailable. In some embodiments, the encapsulated rapamycin provides the rapamycin nanoparticles within a controlled release matrix, forming the encapsulated rapamycin nanoparticle in a single drug delivery structure for oral administration of rapamycin. This encapsulated rapamycin nanoparticle may also be referred to as an enteric-coated rapamycin nanoparticle. In addition, many of the embodiments also include a stabilizing compound (for our purposes, a "stabilizer") within the controlled release matrix either to improve compatibility of the rapamycin with the controlled release matrix, to stabilize the crystalline morphology of the rapamycin, or to help further prevent degradation of the rapamycin, particularly when the encapsulated rapamycin nanoparticle is exposed to air, atmospheric moisture, or room temperature or warmer conditions. Particular embodiments incorporate the stabilizers within each rapamycin nanoparticle, although certain aspects of the invention may be embodied with stabilizers on the surface of the encapsulated rapamycin nanoparticles or otherwise dispersed in the controlled release matrix. To different levels depending on the particular approach used for producing the nanoparticles, with or without other additives, the result is more efficacious for treatment and prevention of genetically-predisposed disorders and age-related disorders, especially in the fields of oncology and neurology in humans and other animals.

Rapid anti-solvent precipitation, or controlled precipitation, is one method of preparing the rapamycin nanoparticles as it provides for minimal manipulation of the rapamycin and exquisite control over nanoparticle size and distribution, and the crystallinity of the rapamycin. Several controlled precipitation methods are known in the art, including rapid solvent exchange and rapid expansion of supercritical solutions, both of which can be implemented in batch or continuous modes, are scalable, and suitable for handling pharmaceutical compounds.

Rapamycin nanoparticles prepared by controlled precipitation methods can be stabilized against irreversible aggregation, Ostwald ripening, and/or reduced dispersibility, by control of colloid chemistry, particle surface chemistry and particle morphology. For example, nanoparticles prepared by antisolvent solidification can be stabilized by ionic and non-ionic surfactants that adsorb to nanoparticle surfaces and promote particle colloid stability through either charge repulsion or steric hindrance, respectively. Moreover, stabilizers can affect nanoparticle crystallinity, which may be used to promote different biodistribution and bioavailability in certain indications.

Rapamycin nanoparticles can consist of molecular rapamycin bound by suitable methods to other nanoparticles. Suitable methods of attaching rapamycin to a nanoparticle carrier or substrate may include physical adsorption through hydrogen van der Waals forces or chemisorption through covalent or ionic bonding. Nanoparticle substrates may be either natural or synthetic, and modified to promote specific interactions with rapamycin. Natural nanoparticles include albumin and other proteins, and DNA. Synthetic nanoparticles include organic and inorganic particulates, micelles, liposomes, dendrimers, hyperbranched polymers, and other compounds.

The rapamycin nanoparticles can be processed by any suitable method, such as by milling, high-pressure atomization, or rapid anti-solvent precipitation. Milling is suitable provided care is taken to minimize both rapamycin degradation and particle agglomeration. Rapamycin degradation can be reduced with the aid of cooling or cryogenic processes. Agglomeration due to the increased surface area and concomitant adhesive forces can be reduced by the use of dispersants during the milling process.

In some embodiments, the rapamycin nanoparticles are sized between about 1 nanometer and about 1 micron. In some embodiments, the rapamycin nanoparticles are less than 1 micron diameter. Such smaller particles provide better control of final particle size, improved stability within the particles, and the ability to tune bioavailability by controlling the crystallinity and composition of the rapamycin nanoparticles.

Manufacturing approaches for the encapsulated rapamycin nanoparticle drug delivery structure embodiments of the present invention include creating a solution of the controlled release matrix, with the rapamycin nanoparticles dispersed therein, in appropriate proportion and producing a heterogeneous mixture. The solvent for such mixtures can be a suitable volatile solvent for the controlled release matrix. In some embodiments, the solvent is either a poor solvent or non-solvent for the rapamycin nanoparticles so that when the rapamycin nanoparticles are dispersed into the controlled release matrix solution they remain as discrete nanoparticles. The resulting dispersion of rapamycin nanoparticles in the controlled release matrix solution can then be reduced to a dry particulate powder by a suitable process, thereby resulting in microparticles of a heterogeneous nature comprised of rapamycin nanoparticles randomly distributed in the controlled release matrix. The particulate powder may also be tailored by a suitable process to achieve a desired particle size for subsequent preparation, which may be from about 20 to about 70 microns in diameter.

The rapamycin nanoparticles are microencapsulated with the controlled release matrix using a suitable particle-forming process to form the encapsulated rapamycin nanoparticle. An example of a particle-forming process is spinning disk atomization and drying. For a detailed discussion of the apparatus and method concerning the aforementioned spin disk coating-process, this application incorporates by references US Patent Applications 2011/221337 and 2011/220430, respectively. Alternatively, for example, the encapsulated rapamycin nanoparticles can be prepared by spray drying.

In some embodiments, not all of the rapamycin nanoparticles will be encapsulated within the controlled release matrix. Instead the rapamycin nanoparticles may be enmeshed with the controlled release matrix, with some of the rapamycin nanoparticles wholly contained within the controlled release matrix while another other rapamycin nanoparticles apparent on the surface of the drug delivery structure, constructed in appearance similar to a chocolate chip cookie.

In some embodiments, and depending on the size of the rapamycin nanoparticles, the encapsulated rapamycin nanoparticles are between 10 and 50 microns in diameter, although diameters as large as 75 microns may be suitable.

The controlled release matrix of the encapsulated rapamycin nanoparticles can be selected to provide desired release characteristics of the encapsulated rapamycin nanoparticles. For example, the matrix may be pH sensitive to provide either gastric release or enteric release of the rapamycin. Enteric release of the rapamycin may achieve improved absorption and bioavailability of the rapamycin. Many materials suitable for enteric release are known in the art, including fatty acids, waxes, natural and synthetic polymers, shellac, and other materials. Polymers are a one enteric coating and may include copolymers of methacrylic acid and methyl methacrylate, copolymers of methyl acrylate and methacrylic acid, sodium alginate, polyvinyl acetate phthalate, and various succinate or phthalate derivatives of cellulose and hydroxypropyl methyl cellulose. Synthetic polymers, such as copolymers of methacrylic acid and either methyl acrylate or methyl methacrylate, are good enteric release polymers due the ability to tune the dissolution pH range of these synthetic polymers by adjusting their comonomer compositions. Examples of such pH sensitive polymers are EUDRAGIT® polymers (Evonik Industries, Essen, Germany). Specifically, EUDRAGIT® S-100, a methyl methacrylate and methacrylic acid copolymer with comonomer ratio of 2:1, respectively, has a dissolution pH of about 7.0, thereby making is suitable for enteric release of rapamycin.

The encapsulated rapamycin nanoparticles may be delivered in various physical entities including a pill, tablet, or capsule. The encapsulated rapamycin nanoparticles may be pressed or formed into a pellet-like shape and further encapsulated with a coating, for instance, an enteric coating. In another embodiment, the encapsulated rapamycin nanoparticles may be loaded into a capsule, also further enterically coated.

Various performance enhancing additives can be added to the encapsulated rapamycin nanoparticles. For example, additives that function as free radical scavengers or stabilizers can be added to improve oxidative and storage stability of the encapsulated rapamycin nanoparticles. In some embodiments, free radical scavengers are chosen from the group that consists of glycerol, propylene glycol, and other lower alcohols. Additives alternatively incorporate antioxidants, such as α-tocopherol (vitamin E), citric acid, EDTA, α-lipoic acid, or the like.

Methacrylic acid copolymers with methyl acrylate or methyl methacrylate are moderate oxygen barriers. Furthermore, these polymers will exhibit an equilibrium moisture content. Oxygen transport due to residual solvent, moisture or other causes, can lead to degradation of the encapsulated rapamycin nanoparticles. Oxygen barrier materials can be added to the encapsulated rapamycin nanoparticles formulation to improve oxygen barrier properties. Oxygen barrier polymers compatible with the polymers are polyvinyl alcohol (PVA) and gelatin.

F. Microparticle and Nanoparticle Rapamycin

Figure 4:
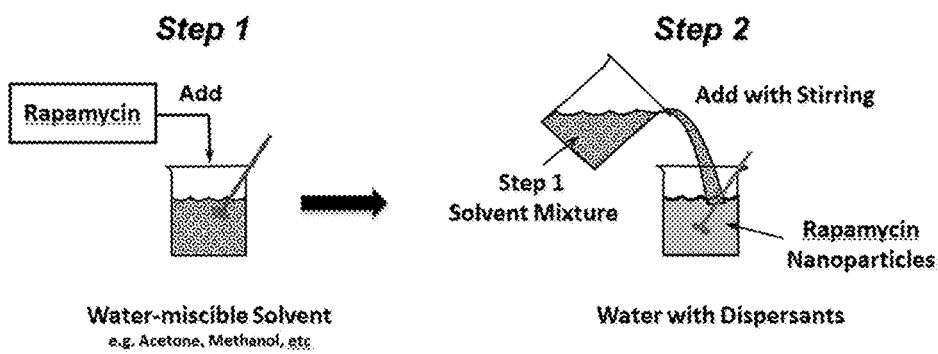
FIG. 4 depicts an embodiment of methods of the present invention, showing a sequence of steps for producing nanoRapa rapamycin nanoparticles by stirring a mixture of a combination of rapamycin and a water-miscible solvent with a combination of water and dispersants.
Figure 5:
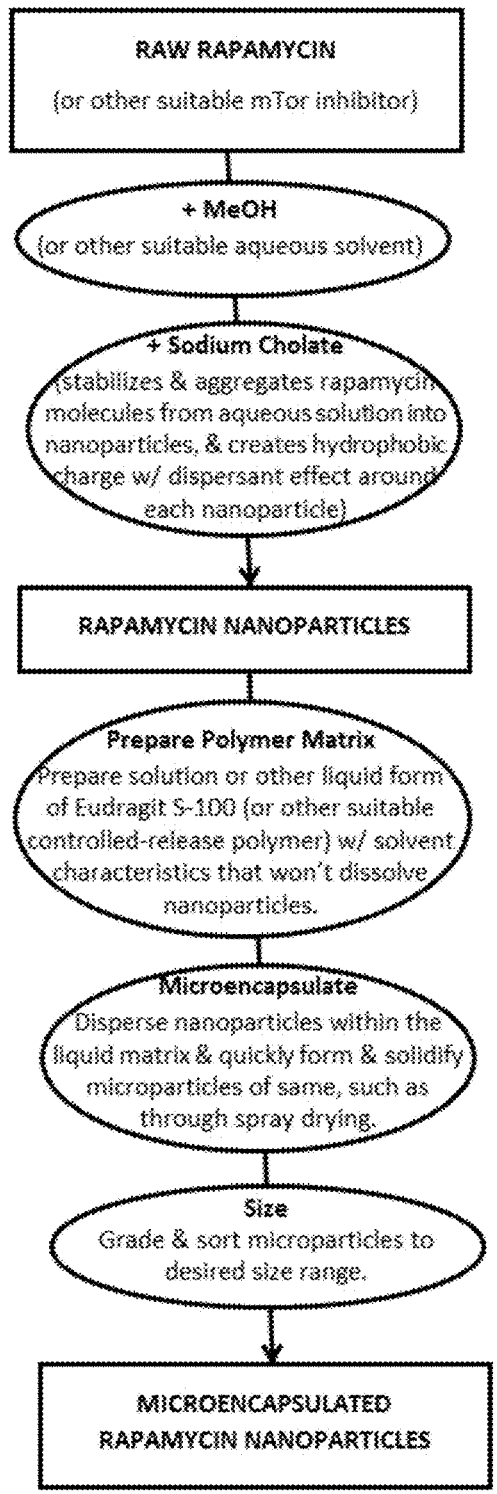
FIG. 5 depicts an embodiment of methods of the present invention, showing a sequence of steps for producing e-nanoRapa microencapsulated nanoparticles of rapamycin.
Figure 6:
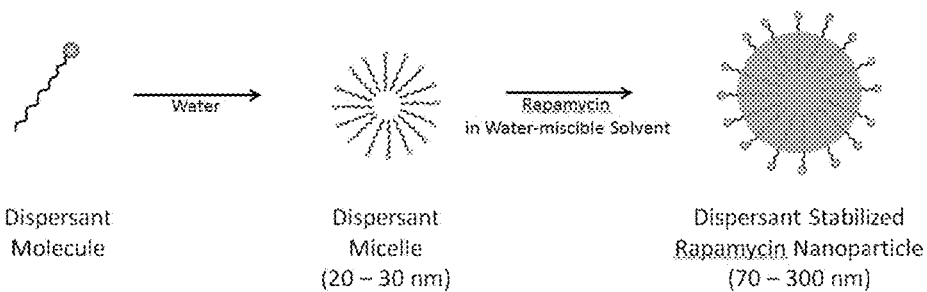
FIG. 6 depicts a nanoRapa embodiment illustrating a detailed view of a micelle created by particular dispersants in solution as is used as part of a sequence of fabricating the nanoRapa rapamycin nanoparticles of FIG. 1.

In some embodiments, rapamycin nanoparticle inclusions comprise discrete nanoparticles of rapamycin heterogeneously dispersed in a controlled release matrix. As illustrated in FIGS. 4-6, the rapamycin nanoparticles are prepared by a suitable method and may contain additives to promote nanoparticle stability, modify rapamycin crystallinity, or promote compatibility of the rapamycin nanoparticles with the controlled release matrix. The controlled release matrix is formulated to promote release of rapamycin to specific parts of the body, such as the intestine, to enhance oxidative and storage stability of the encapsulated rapamycin nanoparticles, and to maintain the discrete, heterogeneously distributed nature of the rapamycin nanoparticles.

Referring to FIG. 4, rapamycin nanoparticles are prepared by anti-solvent precipitation or solidification, also sometimes referred to as controlled precipitation or solidification. Antisolvent solidification is one approach as it provides exquisite control of particle size and distribution, particle morphology, and rapamycin crystallinity. For example, it is possible to prepare nanoparticles with narrow particle size distribution that are amorphous, crystalline, or combinations thereof. Such properties may exhibit additional benefits, by further controlling the biodistribution and bioavailability of rapamycin in specific indications.

Referring now to FIG. 5, rapamycin is dissolved in a suitable water-miscible solvent and then rapidly injected into rapidly stirred water containing an appropriate aqueous soluble dispersant. Water-miscible solvents for rapamycin include methanol, ethanol, isopropyl alcohol, acetone, dimethylsulfoxide, dimethylacetamide, n-methylpyrolidone, tetrahydrofuran, and other solvents. Low boiling point, high vapor pressure water-miscible solvents facilitate their removal during subsequent microparticle formation. Examplary water-miscible solvents are methanol, acetone, and isopropyl alcohol. In some embodiments, the water-miscible solvent is methanol. Some aqueous soluble dispersants include ionic surfactants such as sodium dodecyl sulfate and sodium cholate, non-ionic surfactants such as Pluronics, Poloxomers, Tweens, and polymers, such as polyvinyl alcohol and polyvinylpyrolidone. Examplary aqueous-soluble dispersants are sodium cholate, Pluronic F-68, and Pluronic F-127. In some embodiments, the aqueous-soluble dispersant is sodium cholate, which provides surprisingly beneficial properties. Not only is sodium cholate a surfactant and a dispersant, it serves to cause aggregation of rapamycin particles from the aqueous solution. Moreover, while sodium cholate tends to be a polar molecule as well as an amphoteric surfactant, it surrounds each nanoparticle with a hydrophobic charge when it is enmeshed in the Eudragit matrix. Then, when the nanoparticle is released from the Eudragit matrix within the animal subject's enteric passages where conditions are basic, the same properties cause the nanoparticle to be more readily received and absorbed through the intestinal walls.

Referring to FIG. 6 now, rapamycin is dissolved in the water-miscible solvent at a concentration of about 0.01% w/v to about 10.0% w/v preferably about 0.1% w/v to about 1.0% w/v. The aqueous-soluble dispersant is dissolved in water at a concentration above its critical micelle concentration, or CMC, typically at about 1 to about 10 times the CMC. The rapamycin solution is injected into the aqueous-soluble dispersant solution with agitation at a volumetric ratio of about 1:10 to about 1:1, preferably about 1:5 to about 1:1.

The controlled release matrix is prepared from a water-soluble polymer, which may be a copolymer of methacrylic acid with either methyl acrylate or methyl methacrylate, such as those marketed under the trade name of EUDRAGIT® and having pH-dependent dissolution properties. The controlled release matrix may be comprised of EUDRAGIT® S-100, although other water-soluble enteric controlled release would be suitable. Water-soluble controlled release matrices are selected so as either not to compromise the integrity of rapamycin nanoparticles or to provide a medium in which rapamycin nanoparticles may be prepared by the controlled precipitation methodology described previously.

In preparing the water-soluble polymer it is helpful to maintain conditions that do not compromise the integrity of the rapamycin nanoparticles. Firstly, since the rapamycin nanoparticles are susceptible solubilization by certain co-solvents, it is important to maintain a suitable quantity of certain co-solvents to achieve controlled release matrix solubility while not deleteriously affecting the morphology of the rapamycin nanoparticles. Secondly, rapamycin nanoparticles will be susceptible to chemical degradation by high pH; therefore, it is important to modulate the controlled release matrix solution pH so that rapamycin is not chemically altered. It is helpful the controlled release matrix solution pH be maintained below about pH 8. Lastly, it is helpful to achieve near to complete solubilization of the controlled release matrix in solution so that microencapsulation of the rapamycin nanoparticles by the controlled release matrix in subsequent processing steps may proceed with high efficiency. When using the EUDRAGIT® S-100 as the controlled release matrix, it is helpful to achieve a controlled release matrix solution by using a combination of co-solvents and solution pH modulation. In certain embodiments, the co-solvents are about 40% or less by volume. Similarly, in certain embodiments, the pH of the controlled release matrix solution is about 8 or less, such that the EUDRAGIT® S-100 is not completely neutralized and may be only about 80% or less neutralized. These conditions achieve nearly complete to complete solubilization of the EUDRAGIT® S-100 in a medium that is mostly aqueous and that maintains the integrity of the rapamycin nanoparticles, therefore leading to their microencapsulation by the controlled-release matrix in subsequent processing steps.

The rapamycin nanoparticles prepared by the controlled precipitation method are added to the aqueous solution of the controlled released matrix, resulting in a nanoparticle dispersion in the solubilized controlled release matrix. Alternatively, the rapamycin solubilized in a suitable co-solvent can be dispersed into the aqueous solution of controlled release matrix leading to controlled precipitation of rapamycin particles, thereby leading to a rapamycin nanoparticle dispersion in fewer processing steps, but of appropriate composition to permit subsequent microencapsulation processing.

As an alternative embodiment, the encapsulated rapamycin nanoparticles are created using pre-existing nanoparticle substrates, such as albumin, to create, in the case of albumin, "albumin-rapamycin nanoparticles." Within this general class of alternatives, certain approaches for creating the albumin-rapamycin nanoparticles involve encapsulating rapamycin within albumin nanoparticles or preferentially associating rapamycin with albumin nanoparticles through physical or chemical adsorption. The albumin nanoparticles themselves may be formed from human serum albumin, a plasma protein derived from human serum.

More particularly, this embodiment may involve use of a therapeutic peptide or protein that is covalently or physically bound to albumin, to enhance its stability and half-life. With the albumin stabilized, the rapamycin is mixed with the stabilized albumin in an aqueous solvent and passed under high pressure to form rapamycin-albumin nanoparticles in the size range of 100-200 nm (comparable to the size of small liposomes).

Certain embodiments also address degradation risks and other limits imposed by the related art by preparing encapsulated rapamycin nanoparticles as a heterogeneous mixture of rapamycin nanoparticles in a polymer matrix. Distributed nanoparticles are morphologically different than homogeneous rapamycin; and are less susceptible to degradation because of the bulk nature of the nanoparticles compared to the smaller size of molecular rapamycin.

G. Methods of Using Rapamycin Compositions

"Treatment" and "treating" refer to administration or application of a therapeutic agent to a subject or performance of a procedure or modality on a subject for the purpose of obtaining a therapeutic benefit for a disease or health-related condition. For example, the rapamycin compositions of the present invention may be administered to a subject for the purpose of treating or preventing intestinal adenomas or polyps and cancer in a patient who has been identified as being at risk for developing intestinal polyps or intestinal cancer.

The terms "therapeutic benefit," "therapeutically effective," or "effective amount" refer to the promotion or enhancement of the well-being of a subject. This includes, but is not limited to, a reduction in the frequency or severity of the signs or symptoms of a disease.

"Prevention" and "preventing" are used according to their ordinary and plain meaning. In the context of a particular disease or health-related condition, those terms refer to administration or application of an agent, drug, or remedy to a subject or performance of a procedure or modality on a subject for the purpose of preventing or delaying the onset of a disease or health-related condition. For example, one embodiment includes administering the rapamycin compositions of the present invention to a subject at risk of developing intestinal polyps and cancer (e.g., a patient who has been diagnosed with FAP) for the purpose of preventing intestinal polyps and cancer.

Rapamycin compositions, as disclosed herein, may be used to treat any disease or condition for which an inhibitor of mTOR is contemplated as effective for treating or preventing the disease or condition. For example, methods of using rapamycin compositions to treat or prevent intestinal polyps and cancer in a patient who has been identified as being at risk for developing intestinal polyps or intestinal cancer are disclosed. This risk for developing intestinal polyps or intestinal cancer may be determined by genetic analysis. The treatment or prevention of the disease may be instituted before or after any related surgical intervention such as polypectomy or any form of a full or partial colectomy or colon resection. Dosing regimens may include multiple doses per day, one dose per day, or regular doses one or more days apart.

Other uses of rapamycin compositions as disclosed herein are also contemplated. For example, U.S. Pat. No. 5,100,899 discloses inhibition of transplant rejection by rapamycin; U.S. Pat. No. 3,993,749 discloses rapamycin antifungal properties; U.S. Pat. No. 4,885,171 discloses antitumor activity of rapamycin against lymphatic leukemia, colon and mammary cancers, melanocarcinoma and ependymoblastoma; U.S. Pat. No. 5,206,018 discloses rapamycin treatment of malignant mammary and skin carcinomas, and central nervous system neoplasms; U.S. Pat. No. 4,401,653 discloses the use of rapamycin in combination with other agents in the treatment of tumors; U.S. Pat. No. 5,078,999 discloses a method of treating systemic lupus erythematosus with rapamycin; U.S. Pat. No. 5,080,899 discloses a method of treating pulmonary inflammation with rapamycin that is useful in the symptomatic relief of diseases in which pulmonary inflammation is a component, i.e., asthma, chronic obstructive pulmonary disease, emphysema, bronchitis, and acute respiratory distress syndrome; U.S. Pat. No. 6,670,355 discloses the use of rapamycin in treating cardiovascular, cerebral vascular, or peripheral vascular disease; U.S. Pat. No. 5,561,138 discloses the use of rapamycin in treating immune related anemia; U.S. Pat. No. 5,288,711 discloses a method of preventing or treating hyperproliferative vascular disease including intimal smooth muscle cell hyperplasia, restenosis, and vascular occlusion with rapamycin; and U.S. Pat. No. 5,321,009 discloses the use of rapamycin in treating insulin dependent diabetes mellitus.

H. Pharmaceutical Preparations

Certain methods and compositions set forth herein are directed to administration of an effective amount of a composition comprising the rapamycin compositions of the present invention.

1. Compositions

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it needs to be sterile for such routes of administration as injection.

The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, general safety and purity standards as required by FDA Office of Biologics standards.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media that can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal and nanoparticle formulations; enteric coating formulations; time release capsules; formulations for administration via an implantable drug delivery device, and any other form. One may also use nasal solutions or sprays, aerosols or inhalants in the present invention.

The capsules may be, for example, hard shell capsules or soft-shell capsules. The capsules may optionally include one or more additional components that provide for sustained release.

In certain embodiments, pharmaceutical composition includes at least about 0.1% by weight of the active compound. In other embodiments, the pharmaceutical composition includes about 2% to about 75% of the weight of the composition, or between about 25% to about 60% by weight of the composition, for example, and any range derivable therein.

The compositions may comprise various antioxidants to retard oxidation of one or more components. Additionally, the prevention of the action of microorganisms can be accomplished by preservatives such as various antibacterial and antifungal agents, including but not limited to parabens (e.g., methylparabens, propylparabens), chlorobutanol, phenol, sorbic acid, thimerosal or combinations thereof. The composition should be stable under the conditions of manufacture and storage, and preserved against the contaminating action of microorganisms, such as bacteria and fungi.

In certain embodiments, an oral composition may comprise one or more binders, excipients, disintegration agents, lubricants, flavoring agents, and combinations thereof. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

In particular embodiments, prolonged absorption can be brought about by the use in the compositions of agents delaying absorption, such as, for example, aluminum monostearate, gelatin, or combinations thereof.

2. Routes of Administration

Upon formulation, solutions will be administered in a manner compatible with the dosage formulation and in such amount as is therapeutically effective.

The composition can be administered to the subject using any method known to those of ordinary skill in the art. For example, a pharmaceutically effective amount of the composition may be administered intravenously, intracerebrally, intracranially, intraventricularly, intrathecally, into the cortex, thalamus, hypothalamus, hippocampus, basal ganglia, substantia nigra or the region of the substantia nigra, cerebellum, intradermally, intraarterially, intraperitoneally, intralesionally, intratracheally, intranasally, topically, intramuscularly, intraperitoneally, anally, subcutaneously, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (Remington's, 1990).

In particular embodiments, the composition is administered to a subject using a drug delivery device. Any drug delivery device is contemplated for use in delivering an effective amount of the inhibitor of mTORC1.

3. Dosage

A pharmaceutically effective amount of an inhibitor of mTORC1 is determined based on the intended goal. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

The amount of rapamycin or rapamycin analog or derivative to be administered will depend upon the disease to be treated, the length of duration desired and the bioavailability profile of the implant, and the site of administration. Generally, the effective amount will be within the discretion and wisdom of the patient's physician. Guidelines for administration include dose ranges of from about 0.01 mg to about 500 mg of rapamycin or rapamycin analog.

For example, a dose of the inhibitor of mTORC1 may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. In some embodiments, the two or more doses are the same dosage. In some embodiments, the two or more doses are different dosages. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges. In specific embodiments, the composition may be administered daily, weekly, monthly, annually, or any range therein.

Doses for encapsulated rapamycin (eRapa) and for encapsulated rapamycin nanoparticles may be different. According to certain embodiments, doses are contemplated in a range of more than 50 micrograms and up to (or even exceeding) 200 micrograms per kilogram for daily administration, or the equivalent for other frequencies of administration. Although dosing may vary based on particular needs and preferred treatment protocols according to physician preference, maximum tolerable daily bioavailable dosings (trough levels) for a 28-day duration are about 200 micrograms of rapamycin (or equivalent) per subject kilogram, for both human and canine subjects, although those of ordinary skill would understand that greater dose amount ranges would be tolerable and suitable when administered less often than once per day, and lesser ranges would be tolerable when administered more often than once per day.

In certain embodiments, it may be desirable to provide a continuous supply of a pharmaceutical composition to the patient. This could be accomplished by catheterization, followed by continuous administration of the therapeutic agent. The administration could be intra-operative or post-operative.

4. Secondary and Combination Treatments

Certain embodiments provide for the administration or application of one or more secondary or additional forms of therapies. The type of therapy is dependent upon the type of disease that is being treated or prevented. The secondary form of therapy may be administration of one or more secondary pharmacological agents that can be applied in the treatment or prevention of intestinal polyps or cancer or a disease, disorder, or condition associated with intestinal polyps and cancer in a patient who has been identified as being at risk for developing intestinal polyps or intestinal cancer.

If the secondary or additional therapy is a pharmacological agent, it may be administered prior to, concurrently, or following administration of the inhibitor of mTORC1.

The interval between administration of the inhibitor of mTORC1 and the secondary or additional therapy may be any interval as determined by those of ordinary skill in the art. For example, the inhibitor of mTORC1 and the secondary or additional therapy may be administered simultaneously, or the interval between treatments may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other or within about 6 hours to about 12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the inhibitor of mTORC1.

I. Kits

Kits are also contemplated as being used in certain aspects of the present invention. For instance, a rapamycin composition of the present invention can be included in a kit. A kit can include a container. Containers can include a bottle, a metal tube, a laminate tube, a plastic tube, a dispenser, a pressurized container, a barrier container, a package, a compartment, or other types of containers such as injection or blow-molded plastic containers into which the hydrogels are retained. The kit can include indicia on its surface. The indicia, for example, can be a word, a phrase, an abbreviation, a picture, or a symbol.

Further, the rapamycin compositions of the present invention may also be sterile, and the kits containing such compositions can be used to preserve the sterility. The compositions may be sterilized via an aseptic manufacturing process or sterilized after packaging by methods known in the art.

EXAMPLES

The following examples are included to demonstrate certain non-limiting aspects of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Encapsulated rapamycin, sometimes referred to as eRapa, increases life span in a mouse model of colon cancer, referred to as $Apc^{Min/+}$. This mouse model carries a germ line mutation in one copy of the mouse tumor suppressor gene encoding adenomatous polyposis coli (Apc). Min in $Apc^{Min/+}$ refers to a condition called multiple intestinal neoplasms, which in this mouse model develop very early in life, resulting in a short life span of about 180 days. The cause of death of $Apc^{Min/+}$ mice is usually severe anemia due to bleeding from the multiple neoplastic polyps in the intestine. $Apc^{Min/+}$ mice model in part an inherited condition in humans called familial adenomatous polyposis (FAP).

Familial adenomatous polyposis (FAP) is an autosomal dominant disease caused by mutation of the Adenomatous Polyposis *Coli* (APC) gene, located on chromosome 5 (Kinzler, 1991). This germline defect accelerates the initiation of adenoma-carcinoma, resulting in the development of numerous adenomatous colorectal polyps at a young age. Polyposis inevitably progresses to colorectal cancer if left untreated. Given the predictable development of colorectal cancer in patients with FAP, the safest preventative strategy is surgical resection of the colon when polyposis develops. The two main prophylactic surgeries are colectomy with ileorectal anastomosis (IRA) and proctocolectomy with ileal pouch-anal anastomosis (IPAA) (Vasen, 2008). Genetic screening and endoscopy in concert with prophylactic surgery significantly improved the overall survival of FAP patients. However, less well appreciated by medical providers is the second leading cause of death in FAP, duodenal adenocarcinoma. Nearly 90% of patients with FAP develop duodenal polyps, the precursor lesions of duodenal adenocarcinoma (Wallace, 1998) and 4.5% will develop duodenal adenocarcinoma in their lifetime (Bulow, 2004). In contrast to the colon, prophylactic surgical resection of the ampulla and/or duodenum is accompanied by significant morbidity. Duodenal surgery is currently indicated for patients with severe duodenal polyposis or duodenal carcinoma. This patient population has a strong need for adjuvant therapies to surgery to prevent or reduce the polyp formation and carcinogenesis in the gastro-intestinal track.

Since FAP patients develop polyps that eventually progress to colon cancer, and since $Apc^{Min/+}$ mice develop similar neoplasms, this mouse model (and other containing similar mutations in Apc) are widely used by intestinal cancer researchers.

Showing that eRapa treatment beginning early in life in $Apc^{Min/+}$ mice prevents polyps from developing and progressing to the bleeding stage thereby resulting in a life span equal to and perhaps greater than wild type, normal mice (See FIG. 1-A-2 for comparison to life span of normal, wild type) strongly suggests a similar approach in FAP (and other types of GI cancers) in human patients will be of great benefit.

Figure 1A:
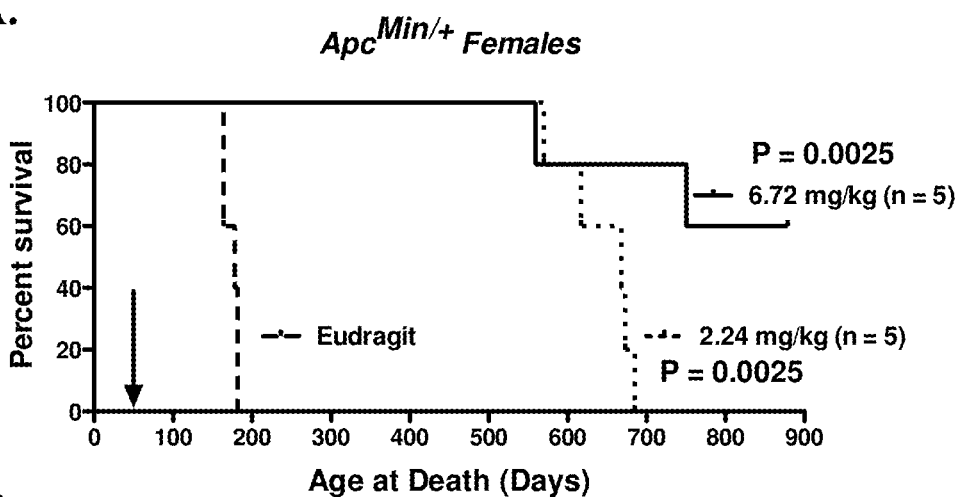
FIGS. 1A-1B Encapsulated rapamycin increases life span and health in $Apc^{Min/+}$ mice. (A) Encapsulated Rapa increases life span in $Apc^{Min/+}$ mice. (B) Life span of rapamycin-treated Apc$^{Min/+}$ mice compared to wild type C57B6 mice or mice treated with RAD001 (everolimus).
Figure 1B:
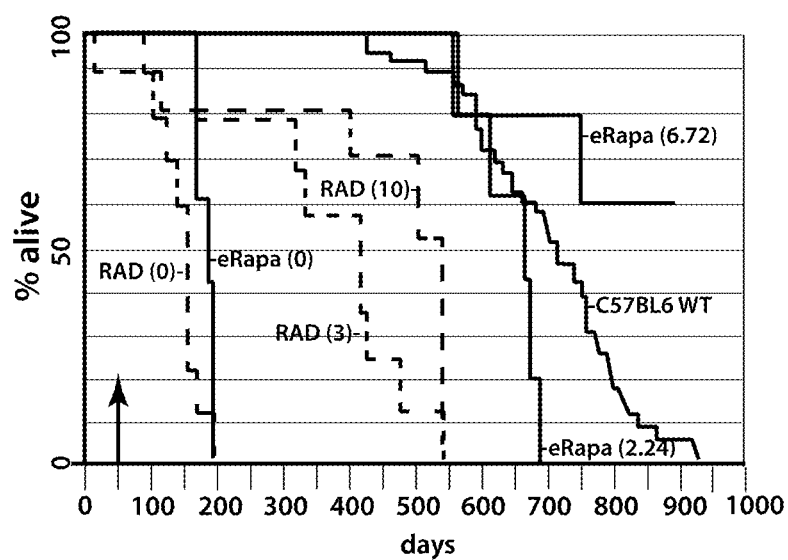

$Apc^{Min/+}$ mice were fed Eudragit control chow (0 ppm rapamycin), a medium dose of 14 ppm encapsulated rapamycin (2.24 mg/kg/day), or a high dose of 42 ppm encapsulated rapamycin (6.72 mg/kg/day) chow beginning at 6 weeks of age (FIG. 1(A), arrow). All mice consuming 0 ppm chow died by 181 days of age, while the rapamycin-treated mice survived to between 570 and 685 days (median 668 days) for the mice dosed at 14 ppm and to between 559 days to 1,093 days (median 937 days). This extension of life span was statistically significant (Logrank Test; p<0.0025) for each dose. FIG. 1(B) In FIG. 1(B), life span of eRapa-treated $Apc^{Min/+}$ mice was compared to wild type C57BL6 mice or mice treated with RAD001 (everolimus), as reported by Fujishita T, Aoki K, Lane H A, Aoki M, Taketo M M in "Inhibition of the mTORC1 pathway suppresses intestinal polyp formation and reduces mortality in $Apc^{\Delta 716}$ mice" (published in Proc. Natl. Acad. Sci. USA, 2008 Sep. 9; 105(36):13544-9). This experiment reveals that eRapa is more effective than the RAD001 treatment because the lower dose of eRapa (2.24 mg/kg) results in a longer life span than the highest dose of RAD001 (10 mg/kg). In addition, 60% of the $Apc^{Min/+}$ mice receiving 42 ppm eRapa diets lived beyond mice treated with the highest dose of RAD001 and wild type, normal mice.

Intestinal polyp counts of $Apc^{Min/+}$ mice at necropsy show a reduction, especially the mice treated with high dose. The first mouse to die in the high dose treatment group showed no visible signs of intestinal neoplasms. The second mouse that died, had three polyps. This is evidence of prevention of neoplastic disease in a highly prone mouse model.

Encapsulated rapamycin also improves the health of the treated mice. The health of the mice was tested by monitoring their activity. Older or sick mice move less than younger, healthy mice. The Nathan Shock Healthspan and Functional Assessment Core of the Barshop Institute for Longevity and Aging Studies documented the activity of the rapamycin-treated and control mice. The data shown in FIG. 2(B) reveal the decline in movement by the 0 ppm fed group (labeled control in the graphs), which has been prevented by both the medium (2.24 mg/kg/day) and high (6.72 mg/kg/day) doses of rapamycin. Both the mid and high dose are equally effective in maintaining this aspect of health. The data shown in FIG. 2(B) also show a difference between movement between light and dark phases of the day cycle for the medium and high doses of rapamycin, the difference being absent in the control 0 ppm dose mice. These data indicate the maintenance of a diurnal rhythm and activity levels similar to wild-type C57BL/6 mice, suggesting better health versus $Apc^{Min/+}$ mice on control chow.

FIG. 2(A) demonstrates that polyp count at the time of death was lower in $Apc^{Min/+}$ mice that were treated with eRapa. The first mouse that died after treatment with 42 ppm eRapa had no polyps, and the second one had only 3 polyps. FIG. 2(C) demonstrates that encapsulated Rapa maintains normal hematocrits in $Apc^{Min/+}$ mice. The hematocrit in eRapa-treated mice (in the high dose group) was normal as compared to wild type C57BL/6 mice (44%) even at 550 days, a time when about 5% of wild type C57BL/6 mice were reported to die from natural causes. It is clear that the high dose eRapa is more effective in maintaining normal hematocrits, which is indicative of the repression of mTORC1 (shown in FIG. 3) and inhibition of polyp development and growth leading to extended longevity in this tumor-prone model.

FIGS. 3(A&B) shows a dose-dependent depression of the phosphorylation of rpS6 by chronic eRapa treatment. rpS6 was recently shown to have a vital role in ribosome biogenesis needed for protein synthesis, development and growth of intestinal neoplasms. Chauvin C, Koka V, Nouschi A, Mieulet V, Hoareau-Aveilla C, Dreazen A, et al, *Oncogene*, 2013. Both mid and high doses are equally effective in repressing this part of mTORC1 downstream signaling.

Also shown are blood levels of rapamycin by the 2.24 mg/kg and 6.72 mg/kg eRapa doses (FIG. 3(C). These blood concentrations are higher than the therapeutic range used for organ transplant recipients. Trepanier D, Gallant H, Legatt D, Yatscoff R. Clin Biochem 1998, 31:345-351. A dose response was observed in proximal and distal small intestine tissue levels of rapamycin, the increase in the distal intestine compared with the proximal, which is consistent with the pH gradient approaching neutrality thereby resulting in an increase drug release by Eudragit delivery. This implies that eRapa may be an effective and convenient method to deliver rapamycin to both the small intestine and blood, indicating that eRapa may have both local and systemic effects.

These data of increased lifespan, increased activity levels, increased hematocrit, dose-dependent depression of the phosphorylation of rpS6, decreased polyp production, and other health indicators is not due exclusively to the dose of rapamycin delivered in the chow. The low dose of 2.24 mg/kg/day is lower than other reported doses of rapamycin such as 3 mg/kg/day and 10 mg/kg/day by oral gavage (Fujishita, et al., *Proc Natl Acad Sci USA*. 105(36):13544-9, 2008) and 40 mg/kg food pellet (Koehl, et al., *Oncogene*, 29:1553-60, 2010). However, and surprisingly, the rapamycin encapsulated in the Eudragit provided a superior therapeutic benefit than rapamycin delivered alone.

The studies described above demonstrate that encapsulated rapamycin in the disclosed formulation, which is enterically delivered, prevents, delays the development of, or slows the growth and progression of intestinal polyps (and subsequent cancer) in this mouse model.

Example 2

Development of methods to produce rapamycin nanoparticles. Rapid solvent exchange was used to examine the formation of rapamycin nanoparticles. Three water-miscible solvents and three water-soluble surfactants were selected to study their respective effects on the formation and morphology of rapamycin nanoparticles. The water-miscible solvents were isopropyl alcohol (Solvent 1), acetone (Solvent 2), and methanol (Solvent 3). The water-soluble surfactants were Pluronic F-68 (Dispersant 1, a non-ionic PEO-PPO-PEO block copolymer), Pluronic F-127 (Dispersant 2, a non-ionic PEO-PPO-PEO block copolymer), and sodium cholate (Dispersant 3, an anionic surfactant). Rapamycin was dissolved in each of the water-miscible solvents at a concentration of 0.25% w/v. The water-soluble surfactants were dissolved in deionized water at concentrations of 0.5% w/v, 0.5% w/v, and 1.0% w/v, respectively, for each of the dispersants. Each experimental combination (e.g. NP-1 to NP-9 in following table) consisted of 5 mL of rapamycin solution and 25 mL of surfactant solution, resulting in a dilution factor of 1:5 solvent:water. 25 mL of surfactant solution was transferred to a 50 mL beaker and stirred with the aid of magnetic mircostirbar. Rapamycin solution was rapidly injected at 500 uL increments with the aid of a micropipette with the pipette tip placed below the surface of the rapidly stirred surfactant solution. The visual appearance of the resulting nanoparticles and their colloidal stability after 24-hours were qualitatively assessed. The following table summarizes the qualities of the rapamycin nanoparticle dispersions. Qualitatively, rapamycin nanoparticle dispersions having a colorless to blue, opalescent appearance will have particle sizes on the order of less than about 300 nm as evidenced by their interaction with the ultraviolet wavelengths of visible light. Whereas, dispersions having a more white appearance will have particle sizes larger than about 300 nm due to their interaction with the broader spectrum of visible light. Rapamycin nanoparticle formulations NP-7 and NP-9 were selected as methods of nanoparticle preparation.

|  | Dispersant 1 | Dispersant 2 | Dispersant 3 |
|---|---|---|---|
| Solvent 1 | NP-1: White, settled, resdispersible | NP-2: Blue, opalescent, settled, redispersible | NP-3: Clear, aggregated, redispersible |
| Solvent 2 | NP-4: Blue, opalescent, some settling | NP-5: White, settled, redispersible | NP-6: Blue, opalescent, settled, redispersible |
| Solvent 3 | NP-7: Blue, opalescent, stable | NP-8: Blue to white, settled, redispersible | NP-9: Blue, opalescent, stable |

Example 3

Preparation of a high concentration rapamycin nanoparticle dispersion. The water-miscible solvent and water-soluble dispersant of NP-9 from Example 1 was used to prepare rapamycin nanoparticles. 656 mg of rapamycin were dissolved in 6.56 mL of Solvent 3 to yield a 1.0% w/v solution. This volume of rapamycin solution was injected into 26.25 mL of 1.0% w/v Dispersant 1 in deionized water. The resulting rapamycin nanoparticle dispersion had a final rapamycin content of 2.4% w/w. The particle size of the dispersion was determined by dynamic light scattering to be 230 nm±30 nm with a single peak.

Example 4

Preparation of a water-soluble enteric coating. 3.5 g of EUDRAGIT® S-100 were added to 70 mL of deionized water with light stirring, resulting in a white dispersion. 1.4 g of sodium hydroxide were added to the dispersion with continued stirring. The resulting dispersion gradually turned clear and colorless indicating an aqueous solution of S-100. The estimated concentration of sodium hydroxide was 0.5N.

Example 5

Preparation of a feedstock containing rapamycin nanoparticles and a water-soluble enteric coating. Rapamycin nanoparticles were prepared as described in Example 2 and then slowly added to an aqueous solution of EUDRAGIT® S-100 prepared as in Example 3. The ratio of rapamycin to S-100 was 1:9, or 10% wt. rapamycin payload. The resulting dispersion was allowed to stir for several minutes to observe stability. After one hour, the dispersion had transformed to a clear yellow, indicating destruction of the rapamycin nanoparticles and a change in the rapamycin. Addition of a small amount of acetic acid to reduce the solution pH to below neutral resulted in a clear, colorless solution.

Example 6

Preparation of water-soluble enteric coating with a water-miscible co-solvent. 3.5 g of EUDRAGIT® S-100 were added to 30/70 v/v methanol/deionized water, resulting in a white dispersion. The dispersion was stirred continuously until a clear solution was formed.

Example 7

Preparation of a feedstock containing rapamycin nanoparticles and a water-soluble enteric coating. Rapamycin nanoparticles were prepared as described in Example 2 and then slowly added to an aqueous solution of EUDRAGIT® S-100 prepared as in Example 5. The ratio of rapamycin to S-100 was 1:9, or 10% wt. rapamycin payload. The white dispersion was allowed to stir for several minutes after which the dispersion was transformed into a clear solution indicating the rapamycin nanoparticles had been destroyed.

Example 8

Preparation of a partially-neutralized, water-soluble enteric coating with a water-miscible co-solvent. 3.5 g of EUDRAGIT® S-100 were added to 10/90 v/v methanol/deionized water, resulting in a white dispersion. The dispersion was titrated to clarity with 2.000 mL of 4.8M sodium hydroxide. The estimated neutralization of the S-100 was 78%.

Example 9

Preparation of a feedstock containing rapamycin nanoparticles and a water-soluble enteric coating. Rapamycin nanoparticles were prepared as described in Example 2 then slowly added to an aqueous solution of EUDRAGIT® S-100 as prepared in Example 7. The ratio of rapamycin to S-100 was 1:9, or 10% wt. rapamycin payload. The resulting white dispersion remained stable for several hours as indicated by no change in color or change in optical clarity. The final pH was 7.5. The particle size of the final dispersion was determined by dynamic light scattering to be 756 nm±52 nm with a single peak and indicating possible clustering of the rapamycin nanoparticles in the resulting feedstock.

Example 10

Preparation of a feedstock containing rapamycin nanoparticles and a water-soluble enteric coating. The rapamycin solution used in Example 2 was injected with stirring into the aqueous solution of EUDRAGIT® S-100 prepared in Example 7. The ratio of rapamycin to S-100 was 1:9, or 10% wt. rapamycin payload. A blue, opalescent colloid was formed and it remained stable for several hours as indicated by no change in color or change in optical clarity. The final pH was 7.5. The particle size of the final dispersion was determined by dynamic light scattering to be 305 nm±60 nm with a single peak.

Example 11

Spray drying of feedstock containing rapamycin nanoparticles and a water-soluble enteric coating. The feedstocks prepared in Examples 8 and 9 were spray dried and analyzed for rapamycin content. Particles prepared from Example 8 had a rapamycin content of 9.5% wt. (87% rapamycin yield). Particles prepared from Example 9 had a rapamycin content of 7.9% wt. (80% rapamycin yield).

Example 12

Storage stability of enteric-coated encapsulated rapamycin nanoparticles. Microparticles prepared by spray drying in Example 10 were stored under controlled conditions at room temperature and 50% relative humidity. Samples were analyzed weekly for rapamycin content. All samples maintained at least 95% of their original rapamycin content at all time points for at least three weeks.

Example 13

Figure 7:
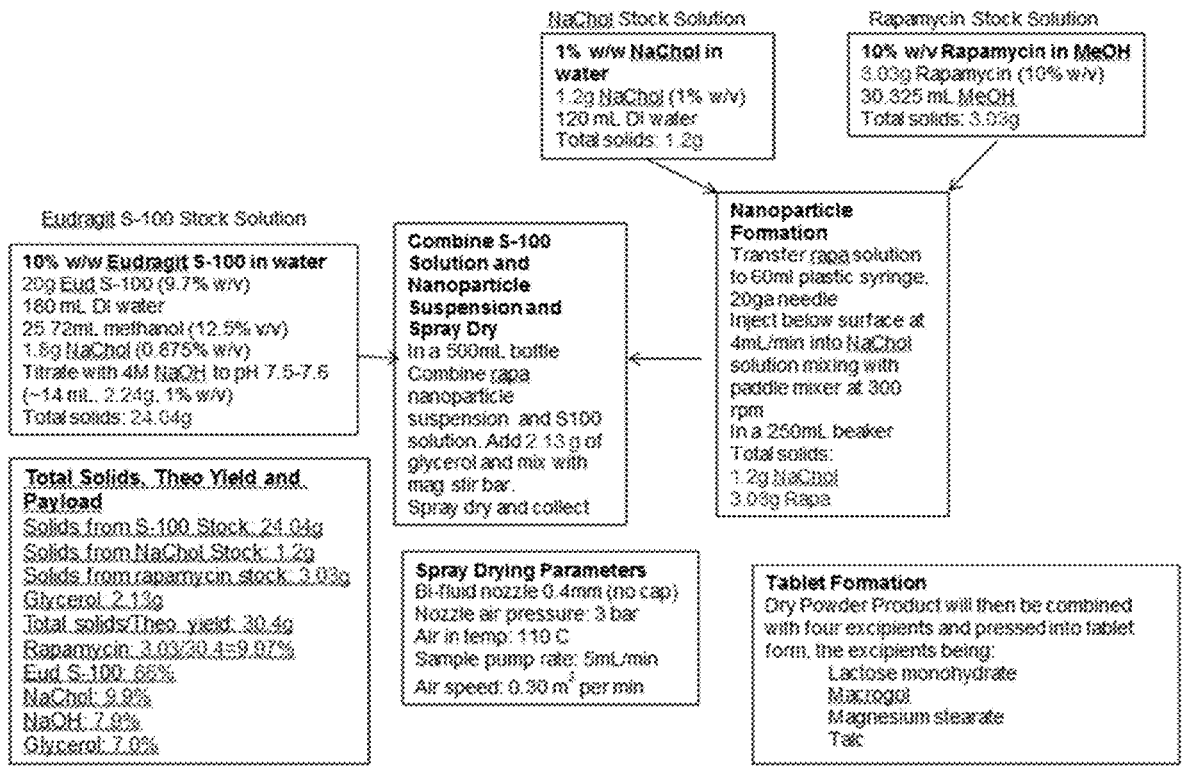
FIG. 7 depicts particular e-nanoRapa embodiments of the invention, particularly with reference to fabrication of e-nanoRapa microencapsulated nanoparticles of rapamycin as produced by the method of FIG. 5.

Preparation of nanoparticles in Eudragit S-100. Referring to FIG. 7, a rapamycin solution was prepared by combining rapamycin with methanol in a 10% w/v ratio as 3.03 g rapamycin and 30.25 ml methanol. A 1% w/w sodium cholate solution was prepared by combining 1.2 g sodium cholate with 120 ml deionized water. Nanoparticle formation was achieved by transferring the rapamycin solution with a 60 ml plastic syringe equipped with a 20 ga needle, injecting the rapamycin solution below the surface of the sodium cholate solution in a 250 ml beaker. Mixing was accomplished with a paddle mixer operating at 300 rpm yielding a rapamycin nanoparticle suspension. A 10% w/w Eudragit S-100 solution was prepared by combining 20 g Eudragit S-100 in a 9.7% w/v mixture with 180 ml deionized water, 25.72 ml methanol in a 12.5% v/v mixture, and 1.8 g sodium cholate in a 0.875% w/v mixture. This 10% w/w Eudragit S-100 solution was titrated with 4M sodium hydroxide to achieve a pH of between about 7.5 and about 7.6. Encapsulated rapamycin particles were then fabricated by combining the Eudragit S-100 solution with the rapamycin nanoparticle suspension. The Eudragit S-100 solution and the rapamycin nanoparticle suspension were combined in a 500 ml bottle, adding 2.13 g of glycerol and mixing with a magnetic stir bar. The combined Eudragit S-100 solution and rapamycin nanoparticle suspension were then spray dried and collected. The spray drying parameters included a 0.4 mm nozzle, nozzle air pressure of 3 bar, input air temperature of 110° C., a sample pump rate of 5 ml/min and an air speed of 0.30 m³/min.

REFERENCES

The following references, to the extent that they provide exemplary procedural or other details supplementary to those set forth herein, are specifically incorporated herein by reference.

Anastas & Moon, *Nat Rev Cancer.* 13: 11-2, 2013
Boulanger, et al., *Am J Transplant.* 8:707-10, 2008.
Bulow, et al., *Gut.* 53(3):381-6, 2004.
Campistol, *Transplantation Proceedings,* 40:S40-3, 2008.
Chauvin, et al., *Oncogene.* Doi: 10.1038/onc.2012.606, 2013.
Cheung, et al., *Oncogene,* 29:1857-64, 2010.
Efeyan & Sabatini, *Curr Opin Cell Biol.* 22(2):169-76, 2009.
Finkel, et al., *Nature.* 448:767-774, 2007.
Fujishita, et al., *Proc Natl Acad Sci USA.* 105(36):13544-9, 2008.
Giardiello, et al., *New England J Med.* 328(18):1313-6, 1993.
Graziani, et al., *Nat Prod Rep.* 26(5):602-9, 2009.

Gregory et al., *Angew Chem Int Ed Engl.* 43(19):2551-3, 2004
Gregory et al., *Org Biomol Chem.* 4(19):3565-8, 2006.
Harrison, et al., *Nature.* 460(7253):392-5, 2009.
Hursting, et al., *Annu Rev Med.* 54:131-52, 2003.
Janus, et al., *Cell Mol Biol Lett.* 10(3):479-98, 2005
Kim, et al., *Best Pract Res Clin Gastroenterol.* 25(4-5):607-22, 2011.
Kinzler, et al., *Science.* 253(5020):661-5, 1991.
Koehl, et al., *Oncogene,* 29:1553-60, 2010.
Korinek, et al., *Science.* 275: 1784-1787, 1997.
Kunstyr, et al., *J Gerontol.* 30(2):157-62, 1975.
Labayle, et al., *Gastroenterology.* 101(3):635-9, 1991
Masoro, *Mech Ageing Dev.* 126: 913-22, 2005.
Miller, et al., *J Gerontol A Biol Sci Med Sci.* 66(2):191-201, 2011
Morin, et al., *Science.* 275: 1787-1790, 1997.
Pallet, et al., *Curr Drug Saf* 1:179-87, 2006.
Rigau, et al., *Ann Int Med.* 115(12):952-4, 1991.
Sankhala, et al., *Targeted Oncol.* 4:135-142, 2009.
Schwecke et al., *Proc Natl Acad Sci USA.* 92(17):7839-43, 1995.
Serruys, et al., *Heart.* 87:305-307, 2002.
Shaw & Cantley, *Nature.* 441:424-30, 2006.
Solomon, et al., *New England J Med.* 352(11):1071-80, 2005.
Sonenberg & Hinnebusch, *Cell.* 136(4):731-45, 2009.
Steinbach, et al., *New England J Med.* 342(26):1946-52, 2000.
Storer, *J Gerontol.* 21(3):404-9, 1966.
U.S. Pat. No. 3,993,749
U.S. Pat. No. 4,316,885
U.S. Pat. No. 4,401,653
U.S. Pat. No. 4,885,171
U.S. Pat. No. 5,023,262
U.S. Pat. No. 5,023,263
U.S. Pat. No. 5,023,264
U.S. Pat. No. 5,078,999
U.S. Pat. No. 5,080,899
U.S. Pat. No. 5,100,883
U.S. Pat. No. 5,100,899
U.S. Pat. No. 5,102,876
U.S. Pat. No. 5,118,677
U.S. Pat. No. 5,118,678
U.S. Pat. No. 5,120,725
U.S. Pat. No. 5,120,726
U.S. Pat. No. 5,120,727
U.S. Pat. No. 5,120,842
U.S. Pat. No. 5,130,307
U.S. Pat. No. 5,138,051
U.S. Pat. No. 5,151,413
U.S. Pat. No. 5,162,333
U.S. Pat. No. 5,164,399
U.S. Pat. No. 5,169,851
U.S. Pat. No. 5,177,203
U.S. Pat. No. 5,194,447
U.S. Pat. No. 5,202,332
U.S. Pat. No. 5,206,018
U.S. Pat. No. 5,221,670
U.S. Pat. No. 5,221,740
U.S. Pat. No. 5,233,036
U.S. Pat. No. 5,260,299
U.S. Pat. No. 5,260,300
U.S. Pat. No. 5,262,423
U.S. Pat. No. 5,262,424
U.S. Pat. No. 5,288,711
U.S. Pat. No. 5,302,584
U.S. Pat. No. 5,310,903
U.S. Pat. No. 5,321,009
U.S. Pat. No. 5,344,833
U.S. Pat. No. 5,346,893
U.S. Pat. No. 5,358,944
U.S. Pat. No. 5,362,718
U.S. Pat. No. 5,373,014
U.S. Pat. No. 5,378,696
U.S. Pat. No. 5,378,836
U.S. Pat. No. 5,385,908
U.S. Pat. No. 5,385,909
U.S. Pat. No. 5,385,910
U.S. Pat. No. 5,389,639
U.S. Pat. No. 5,391,730
U.S. Pat. No. 5,411,967
U.S. Pat. No. 5,434,260
U.S. Pat. No. 5,446,048
U.S. Pat. No. 5,463,048
U.S. Pat. No. 5,480,988
U.S. Pat. No. 5,484,790
U.S. Pat. No. 5,484,791
U.S. Pat. No. 5,486,522
U.S. Pat. No. 5,486,523
U.S. Pat. No. 5,486,524
U.S. Pat. No. 5,488,054
U.S. Pat. No. 5,489,595
U.S. Pat. No. 5,489,680
U.S. Pat. No. 5,491,231
U.S. Pat. No. 5,504,091
U.S. Pat. No. 5,504,204
U.S. Pat. No. 5,504,291
U.S. Pat. No. 5,508,285
U.S. Pat. No. 5,508,286
U.S. Pat. No. 5,508,290
U.S. Pat. No. 5,508,399
U.S. Pat. No. 5,516,780
U.S. Pat. No. 5,519,031
U.S. Pat. No. 5,521,194
U.S. Pat. No. 5,525,610
U.S. Pat. No. 5,530,007
U.S. Pat. No. 5,530,121
U.S. Pat. No. 5,532,355
U.S. Pat. No. 5,541,191
U.S. Pat. No. 5,541,192
U.S. Pat. No. 5,550,133
U.S. Pat. No. 5,559,112
U.S. Pat. No. 5,559,119
U.S. Pat. No. 5,559,120
U.S. Pat. No. 5,559,122
U.S. Pat. No. 5,561,138
U.S. Pat. No. 5,563,145
U.S. Pat. No. 5,567,709
U.S. Pat. No. 5,637,590
U.S. Pat. No. 5,637,590
U.S. Pat. No. 5,665,772
U.S. Pat. No. 5,780,462
U.S. Pat. No. 5,912,253
U.S. Pat. No. 5,922,730
U.S. Pat. No. 5,955,457
U.S. Pat. No. 5,985,890
U.S. Pat. No. 6,004,973
U.S. Pat. No. 6,015,809
U.S. Pat. No. 6,399,625
U.S. Pat. No. 6,440,990
U.S. Pat. No. 6,670,355
U.S. Pat. No. 6,677,357
U.S. Pat. No. 6,680,330

U.S. Pat. Pub. 2004/0010002
U.S. Pat. Pub. 2006/0264453
U.S. Pat. Pub. 2007/0142423
U.S. Pat. Pub. 2007/0203168
U.S. Pat. Pub. 2007/0203169
U.S. Pat. Pub. 2007/0203170
U.S. Pat. Pub. 2007/0203171
U.S. Pat. Pub. 2007/0203172
U.S. Pat. Pub. 2007/0225313
U.S. Pat. Pub. 2007/0280992
U.S. Pat. Pub. 2008/0069797
U.S. Pat. Pub. 2008/0085880
U.S. Pat. Pub. 2008/0091008
U.S. Pat. Pub. 2008/0182867
U.S. Pat. Pub. 2008/0188511
U.S. Pat. Pub. 2008/0249123
Ulrich, et al., *Am J Transplant.* 8:2192-8, 2008.
Vasen, et al., *Gut.* 57(5):704-13, 2008.
Wallace & Phillips, *Br J Surg.* 85(6):742-50, 1998.
Wijnhoven, et al., *DNA Repair (Amst).* 4(11):1314-24, 2005.
Yu, et al., *Exp Clin Transplant.* 6:113-7, 2008.
Zell, et al., *Cancer Prev Res.* 2(3):209-12, 2009.
Zoncu, et al., *Nat Rev Mol Cell Biol.* 12:21-35, 2010.

The invention claimed is:

1. A method for extending life span expectancy in a human patient with familial adenomatous polyposis (FAP), wherein the method comprises administering an effective amount of a composition comprising discrete dispersant-stabilized nanoparticles of rapamycin or an analog thereof, wherein the dispersant comprises sodium cholate, wherein said discrete dispersant-stabilized nanoparticles of rapamycin or an analog thereof are encapsulated and heterogeneously dispersed in an enteric coating, and wherein the analog of rapamycin is selected from the group consisting of everolimus, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, 42-0-(2-hydroxy) ethyl rapamycin, or rapamycin oximes, rapamycin aminoesters, rapamycin dialdehydes, 0-alkylated rapamycin derivatives, rapamycin amidino carbamates, biotin esters of rapamycin, carbamates of rapamycin, rapamycin hydroxyesters, rapamycin 42-sulfonates and 42-(N-carbalkoxy)sulfamates, rapamycin oxepane isomers, imidazolidyl rapamycin derivatives, rapamycin alkoxyesters, rapamycin pyrazoles, rapamycin amide esters, rapamycin fluorinated esters, rapamycin acetals, oxorapamycins, and rapamycin silyl ethers.

2. The method of claim 1, wherein said enteric coating comprises cellulose acetate succinate, hydroxy propyl methyl cellulose phthalate co-polymer, or a polymethacrylate-based copolymer selected from the group consisting of a methyl acrylate-methacrylic acid copolymer, and a methyl methacrylate-methacrylic acid copolymer.

3. The method of claim 2, wherein the coating comprises poly(methacrylic acid-co-ethyl acrylate) in a 1:1 ratio, poly(methacrylic acid-co-ethyl acrylate) in a 1:1 ratio, poly(methacrylic acid-co-methyl methacrylate) in a 1:1 ratio, poly(methacylic acid-co-methyl methacrylate) in a 1:2 ratio, poly(methyl acrylate-co-methyl methacrylate-co-methacrylic acid) in a 7:3:1 ratio, poly(ethyl acrylate-co-methyl methacrylate-co-trimethylammonioethyl methacrylate chloride) in a 1:2:0.2 ratio, poly (ethyl acrylate-co-methyl methacrylate-co-trimethylammonioethyl methacrylate chloride) in a 1:2:0.1 ratio, or poly(butyl methacrylate-co-(2-dimethylaminoethyl) methacrylate-co-methyl methacrylate) in a 1:2:1 ratio, a naturally-derived polymer, or a synthetic polymer, or any combination thereof.

4. The method of claim 1, wherein the patient has been diagnosed with an inflammatory bowel disease, an intestinal polyp, or an adenoma, or as having a mutation that is known to cause increased WNT signaling.

5. The method of claim 1, wherein the patient has a family history of intestinal polyps or intestinal cancer.

6. The method of claim 1, wherein the patient is between the ages of 1 to 18 years, 18 years to 50 years, or over the age of 50 years.

7. The method of claim 1, wherein the composition comprises, in discrete dispersant-stabilized nanoparticles, rapamycin or an analog thereof at a concentration of 0.001 mg to 30 mg of rapamycin or analog thereof total per dose, or 0.001% to 60% by weight of rapamycin or an analog thereof.

8. The method of claim 1, wherein the average blood level of rapamycin or analog thereof in the subject is greater than 0.5 ng of rapamycin or analog thereof per mL whole blood after administration of the composition.

9. The method of claim 1, wherein the composition is administered orally, enterically, colonically, anally, intravenously, or dermally with a patch.

10. The method of claim 1, wherein the discrete dispersant-stabilized nanoparticles of rapamycin or analog thereof are to be administered in two or more doses.

11. The method of claim 10, wherein the interval of time between administration of doses comprising discrete dispersant-stabilized nanoparticles of rapamycin or an analog thereof is 0.5 to 30 days, preferably 1 to 15 days, preferably 1 to 7 days, more preferably 1 to 5 days, more preferably 1 to 3 days, most preferably 0.5 to 1 day.

12. The method of claim 1, wherein the composition further comprises a second active agent selected from the group consisting of metformin, celecoxib, eflornithine, sulindac, ursodeoxycholic acid, an anti-inflammatory agent, an anti-autoimmune agent, and a cytotoxic or cytostatic anti-cancer agent.

13. The method of claim 12, wherein the composition comprising discrete dispersant-stabilized nanoparticles of rapamycin or an analog thereof is to be administered at the same time, before or after as the composition comprising the second active agent.

14. The method of claim 13, wherein the interval of time between administration of the composition comprising discrete dispersant-stabilized nanoparticles of rapamycin or an analog thereof and the composition comprising the second active agent is 1 to 30 days.

15. The method of claim 1, wherein the composition comprising discrete dispersant-stabilized nanoparticles of rapamycin or an analog thereof prevents the development of new adenomas or polyps.

16. The method of claim 1, wherein the composition comprising discrete dispersant-stabilized nanoparticles of rapamycin or an analog thereof decreases the number or severity of adenomatous polyps.

17. The method of claim 1, wherein the composition comprising discrete dispersant-stabilized nanoparticles of rapamycin or an analog thereof induces a reduction in size or number of existing adenomas or polyps.

18. The method of claim 1, wherein the composition comprising discrete dispersant-stabilized nanoparticles of rapamycin or an analog thereof prevents the conversion of adenomas or polyps into adenocarcinomas and cancer tissue.

19. The method of claim 1, wherein the composition comprising discrete dispersant-stabilized nanoparticles of rapamycin or an analog thereof prevents adenomas or polyps from converting into malignant cancer that spread into other bodily tissues, organs and blood systems in a patient that has been diagnosed as having intestinal adenomas, polyps or FAP.

20. The method of claim 3, wherein the naturally-derived polymer is selected from the group consisting of alginates and their various derivatives, chitosans and their various derivatives, carrageenans and their various analogues, celluloses, gums, gelatins, pectins, gellans, polyethyleneglycols (PEGs) and polyethyleneoxides (PEOs), acrylic acid homo- and copolymers with acrylates and methacrylates, homopolymers of acrylates and methacrylates, polyvinyl alcohol (PVOH), and polyvinyl pyrrolidone (PVP).

* * * * *